US012667339B2

(12) United States Patent (10) Patent No.: US 12,667,339 B2

Osumi et al. (45) Date of Patent: Jun. 30, 2026

(54) MEDICAL IMAGE DIAGNOSIS SYSTEM AND CONTROL METHOD THEREOF

(71) Applicant: Canon Kabushiki Kaisha, Tokyo (JP)

(72) Inventors: Ryota Osumi, Nasushiobara (JP); Takatoshi Okumura, Yaita (JP); Eric Nguyen, Cesson-Sevigne (FR); Lionel Le Scolan, Cesson-Sevigne (FR); Falk Tannhauser, Cesson-Sevigne (FR)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/672,199

(22) Filed: May 23, 2024

(65) Prior Publication Data

US 2024/0389982 A1 Nov. 28, 2024

(30) Foreign Application Priority Data

May 24, 2023 (JP) ................................. 2023-085805

(51) Int. Cl.
*A61B 8/08* (2006.01)
*A61B 8/00* (2006.01)

(52) U.S. Cl.
CPC ............ *A61B 8/5207* (2013.01); *A61B 8/463* (2013.01)

(58) Field of Classification Search
CPC ..... A61B 8/5207; A61B 8/463; A61B 8/4405; A61B 8/5223; G01R 33/546; G06T 7/0012
See application file for complete search history.

(56) References Cited

U.S. PATENT DOCUMENTS

| | | | |
|---|---|---|---|
| 9,468,420 B2 | 10/2016 | Wahrenberg | |
| 2013/0188854 A1* | 7/2013 | Bilgic | ................... A61B 5/055 |
| | | | 382/131 |

(Continued)

FOREIGN PATENT DOCUMENTS

| | | | |
|---|---|---|---|
| JP | 2004-16612 A | | 1/2004 |
| JP | 2004016612 A | * | 1/2004 |

(Continued)

OTHER PUBLICATIONS

Koyama, et al. "Sequential Line Search for Efficient Visual Design Optimization by Crowds", ACM Transactions on Graphics, vol. 36, No. 4, Jul. 2017, pp. 1-11.

(Continued)

*Primary Examiner* — Kaitlyn E Sebastian
(74) *Attorney, Agent, or Firm* — Oblon, McClelland, Maier & Neustadt, L.L.P.

(57) ABSTRACT

The medical image diagnosis system comprises processing circuitry configured to set values of an image quality indicator selected by a user regarding multiple types of the image quality indicator to display a medical image as an anchor, and generate a first thumbnail image based on the anchor; cause a display to display the first thumbnail image; generate a plurality of second thumbnail images by respectively increasing or decreasing the multiple types of the image quality indicator from the anchor; cause the display to display the plurality of second thumbnail images; calculate a new image quality indicator adjusted with a variable step width; and generate a new first thumbnail image by using a new anchor, display the new first thumbnail image, generate a plurality of new second thumbnail images based on the values of the new image quality indicator, and display the plurality of new second thumbnail images.

15 Claims, 13 Drawing Sheets

(56) References Cited

U.S. PATENT DOCUMENTS

| | | | | |
|---|---|---|---|---|
| 2014/0328526 | A1* | 11/2014 | Wahrenberg | A61B 8/0866 |
| | | | | 382/131 |
| 2020/0268350 | A1* | 8/2020 | Yoshiara | G06T 7/0012 |

FOREIGN PATENT DOCUMENTS

| | | | |
|---|---|---|---|
| JP | 6608126 | B2 | 11/2019 |
| JP | 2020-74996 | A | 5/2020 |
| JP | 2020-159789 | A | 10/2020 |

OTHER PUBLICATIONS

Kim, et al., "Ultrasound Design Gallery: Personalized Enhancement of Medical Ultrasound Images with Preferential Bayesian Optimization", Pre-print Under review Nov. 2021, pp. 1-17.
Koyama, et al., "Sequential Gallery for Interactive Visual Design Optimization", ACM Trans. Graph., vol. 39, No. 4, Aug. 2020, pp. 1-12.

* cited by examiner

100

103

104

102

101

MEDICAL IMAGE DIAGNOSIS SYSTEM AND CONTROL METHOD THEREOF

CROSS REFERENCE TO RELATED APPLICATIONS

This application is based upon and claims the benefit of priority from the prior Japanese Patent Application No. 2023-085805, filed on May 24, 2023, the entire contents of which are incorporated herein by reference.

FIELD

The embodiments disclosed in the specification and drawings relate to a medical image diagnosis system and a control method thereof.

BACKGROUND

Many types of medical image diagnosis system, such as an ultrasonic diagnosis system, a Magnetic Resonance Imaging (MRI) system, an X-ray Computed Tomography (CT) system, or a Positron Emission Tomography (PET) system allow a user to adjust an image quality of a medical image based on user preferences.

However, there are many image quality indicators to control the image quality, which makes it difficult for a user of the medical image diagnosis system to adjust values of a plurality of image quality indicators and reach an optimal image quality. For instance, there are 60 types of image quality indicators that contributes to an image quality adjustment for a preset image processing, and if there are 5 levels of adjustment values for each image quality indicator to be selected or set from, 5 to a power of 60 combinations of adjustment settings may be generated. Likewise, even if N types of contributory image quality indicator are sorted from numerous image quality indicators, adjustment is still difficult since an N-dimension adjustment is required. Thus, in many medical image diagnosis systems, several combinations of the image quality indicator are indexed according to the user preference, and index values be adjustable in several levels as a Graphical User Interface (GUI) of a system. However, a degree of freedom of adjusting the image quality becomes quite limited when the combination of image quality indicator is indexed as such.

There also are medical image diagnosis systems which allow the user to select the image quality indicator and adjust the values of the image quality indicator while viewing an image. Regarding these medical image diagnosis systems, a plurality of thumbnail images rendered according to each of a plurality of rendering conditions and a rendering image rendered according to a preset rendering condition are generated. If the plurality of thumbnail images generated from this method is displayed as an operating button on a touch command screen, it is visually easier to understand than adjusting the image quality indicator with numerical inputs or knob operations. However, a step width of the values of the image quality indicator might be fixed when respectively adapting the plurality of thumbnail images to the plurality of rendering conditions and displaying them. In such case, if the step width is large, the optimal image quality might be missed, and if the step width is small, it takes time and effort to reach the optimal image quality. In other words, when the step width of image quality adjustment is fixed, it is difficult to quickly reach the optimal image quality.

There also are medical image diagnosis systems that optimizes an unknown perceptual coefficient with Bayesian optimization by decomposing each of the plurality of image quality indicators into a 1-dimensional slider operation, and presenting them to the user, which allow the user to adjust the values of the image quality indicator while viewing the image. In such medical image diagnosis systems, the image quality adjustment in each dimension may continuously change, but it is difficult to apply on methods that adjust the values of the image quality indicator by selecting thumbnail images.

There also are medical image diagnosis systems that optimizes a value of the image quality indicator with Bayesian optimization by estimating the user's recognition for the image quality, and presenting a User Interface (UI) capable of adjusting one type of image quality indicator, which allow the user to adjust the image quality indicator while viewing the image. Since it is impossible to simultaneously adjust the plurality of image quality indicators and since the image quality indicator in each dimension continuously changes in such medical image diagnosis systems, it is difficult to apply on methods that adjust the values of the image quality indicator by selecting thumbnail images.

Furthermore, there are medical image diagnosis systems that decompose an N-dimensional image quality search query into a series of subtasks of 2-dimensional image quality search queries, which allow the user to select the image quality indicator for each subtask with thumbnails mapped in 2-dimension. In such medical image diagnosis systems, conversion from N-dimension to 2-dimension may be formalized as a general method applicable to various image quality indicators. However, it is clinically desirable for the conversion to each image quality indicator in the medical image to be formalized for each image quality indicator. Thus, when the conversion from N-dimension to 2-dimension is formalized as the general method to be applied on various image quality indicators, the difficulty of reaching the optimal image quality is still not resolved.

DETAILED DESCRIPTION

With reference to the drawings below, embodiments of a medical image diagnosis system and a control method thereof will be described. In the description below, same reference signs are given for components substantially identical in terms of configuration and function and duplicate description will be given only when necessary.

Figure 1:
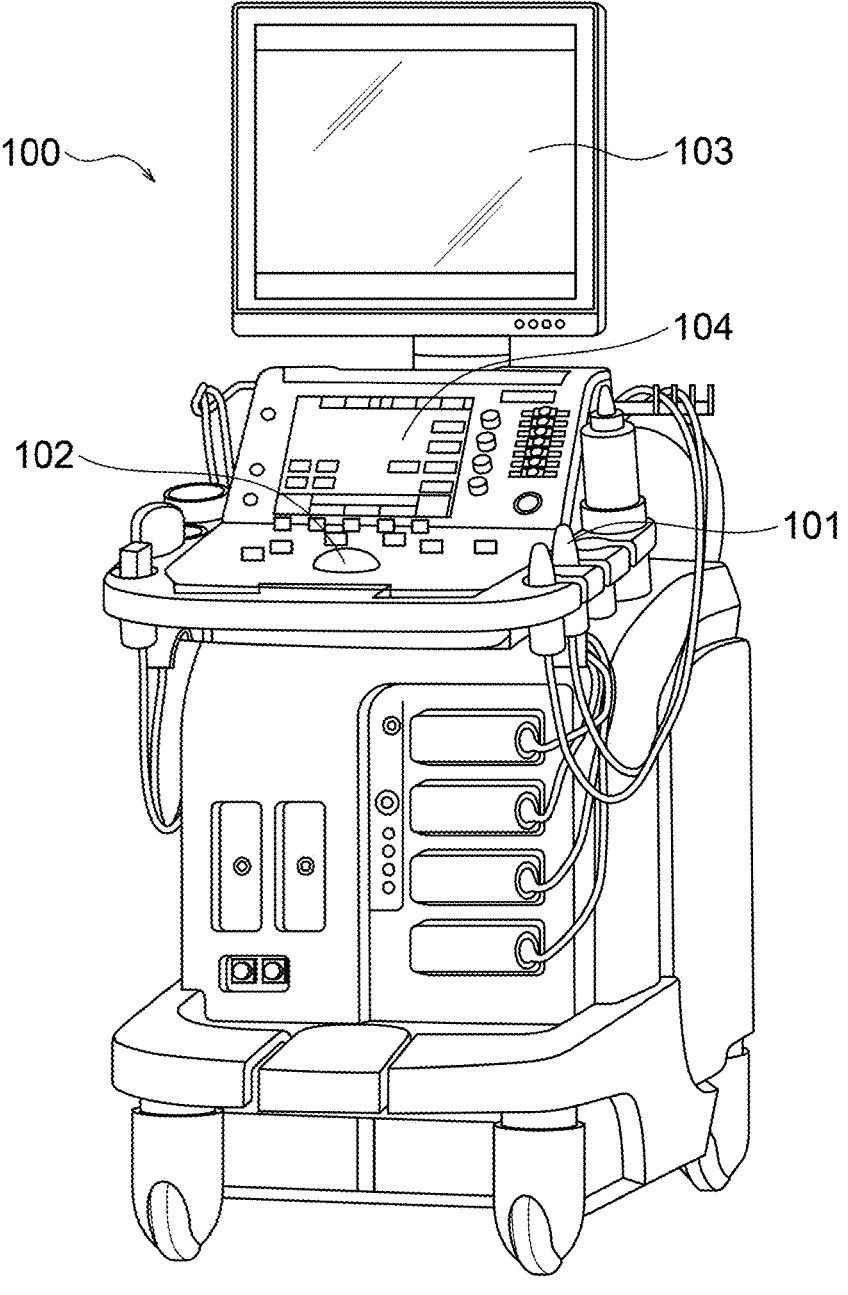
FIG. 1 is a perspective view illustrating a whole exemplary configuration of a medical image diagnosis system according to a first embodiment.
Figure 2:
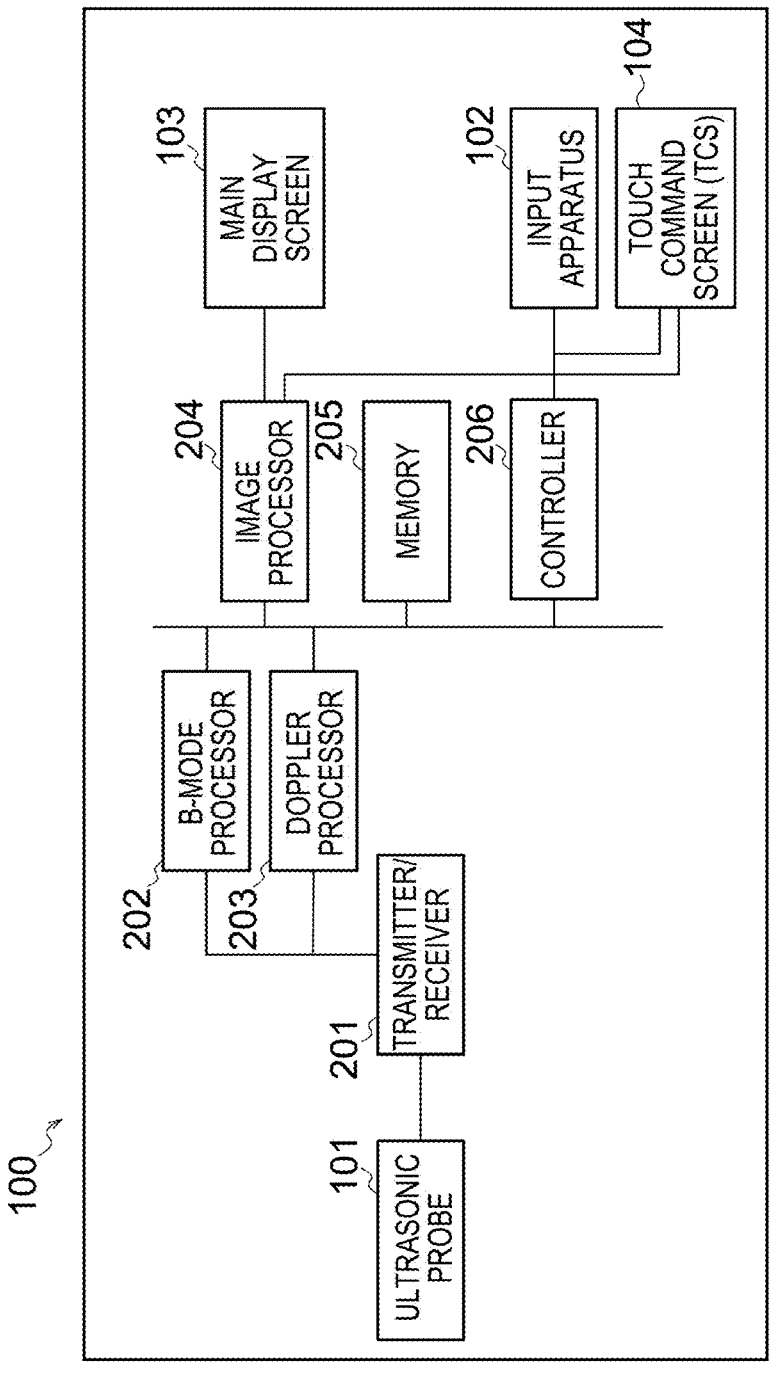
FIG. 2 is a diagram illustrating an exemplary block configuration diagram of the medical image diagnosis system shown in FIG. 1.

FIG. 1 is a perspective view illustrating a whole exemplary configuration of a medical image diagnosis system 100 according to a first embodiment. The medical image diagnosis system 100 shown in FIG. 1 may be configured by an ultrasonic diagnosis system. FIG. 2 illustrates an exemplary block configuration diagram of the medical image diagnosis system 100 shown in FIG. 1.

As shown in FIG. 1, the medical image diagnosis system 100 according to the present embodiment comprises an ultrasonic probe 101, an input apparatus 102, a main display screen 103, and a touch command screen (TCS) 104. Further, as shown in FIG. 2, the medical image diagnosis system 100 further comprises a transmitter/receiver 201, a B-mode processor 202, a doppler processor 203, an image processor 204, a memory 205, and a controller 206 inside.

The ultrasonic probe 101 is a device (probe) which irradiates an ultrasonic signal to a subject and detects the ultrasonic signal reflected from the subject, formed of an electrically/mechanically reversible conversion element. This ultrasonic probe 101 may be configured by a phased array type probe which equips on its tip a plurality of elements arranged in an array. By this, the ultrasonic probe 101 converts a supplied pulse drive voltage into the ultrasonic signal to transmit it to a desired direction within a scan region of the subject and converts the ultrasonic signal reflected from the subject into an echo signal of a corresponding voltage thereto.

Note that the ultrasonic probe 101 may be an 1D array probe which scans the subject in 2-dimention, or a 3-dimentional probe which scans the subject in 3-dimention, i.e., a mechanical 4D probe or a 2D array probe. When the 3-dimentional probe is used, a specific tomographic image or a multi planar reconstruction (MPR) image is included on a medical image displayed on the main display screen 103.

The transmitter/receiver 201 has a trigger generation circuitry, a delay circuitry, and a pulsar circuitry etc., and supplies a drive signal to the ultrasonic probe 101. The pulsar circuitry repeatedly generates, at a preset rate frequency, a rate pulse for forming the ultrasonic signal to be transmitted. Likewise, the delay circuitry applies a delay time for every piezoelectric transducer, necessary to converge the ultrasonic signal generated from the ultrasonic probe 101 into a beam and determine a transmission directivity, to each rate pulse generated by the pulsar circuitry. Further, the trigger generation circuitry applies the drive signal (drive pulse) to the ultrasonic probe 101 at timings based on the rate pulse. In other words, the delay circuitry arbitrarily adjusts a transmission direction from a piezoelectric transducer surface by varying the delay time applied to each rate pulse.

Note that the transmitter/receiver 201 comprises a function that may instantaneously change a transmitting frequency or a transmitting drive voltage etc. to execute a preset scan sequence based on a command from the controller 206, which will be described below. Especially, a change of a transmitting drive voltage is realized by a transmission circuitry which may instantaneously switch the value or a mechanism which electrically switches a plurality of power source units.

Likewise, the transmitter/receiver 201 also comprises an amplifier circuitry, A/D converter, an adder etc., and generates a reflected wave data by performing various processing to the ultrasonic signal, which is the reflected wave received by the ultrasonic probe 101. The amplifier circuitry performs a gain correction processing by amplifying the ultrasonic signal, which is the reflected wave, for every channel. The A/D converter generates digital data by A/D converting the ultrasonic signal, which is the gain corrected reflected wave, and applies the delay time necessary to determine a receiving directivity to the digital data. The adder generates the reflected wave data by performing an adding process of the digital data generated by the A/D converter. A reflective component from a direction corresponding to the receiving directivity of the ultrasonic signal, which is the reflective wave, is enhanced by the adding process of the adder.

Note that a method of transmitting/receiving by the transmitter/receiver 201 may be a method transmitting/receiving a plane wave, instead of the method converging the ultrasonic signal into a beam as in the description above.

The B-mode processor 202 performs a logarithmic amplification, an envelope detection processing, a logarithmic compression, etc., to the reflected wave data from the transmitter/receiver 201 to generate B-mode information where each signal intensity at multiple sample points is expressed as a change of luminance.

The Doppler processor 203 performs a color Doppler method on the reflected wave data from the transmitter/receiver 201 and computes a blood flow information, i.e., a Doppler information. In the color Doppler method, transmitting/receiving the ultrasonic signal is performed multiple times on a same scan line, suppressing a signal (clutter signal) originating from a stationary tissue or a slow-moving tissue by applying an MTI (Moving Target Indicator) filter to a data array in a same location, and a signal originating from a blood flow is extracted. Then, in the color Doppler method, the Doppler information such as a blood flow velocity, a blood flow dispersion, a blood flow power etc., is estimated from the blood flow signal.

The image processor 204 converts a scanning system of the B-mode information and the Doppler information into a scanning system suitable for display (scan conversion) and generates an ultrasonic diagnosis image as the medical image. Information indicating a composition, parallelism, and display position of each image information, furthermore various information to assist an operation of the medical image diagnosis system 100, which is the ultrasonic diagnosis system, and a supplementary information necessary for ultrasonic diagnosis of patient information etc. are generated together with the ultrasonic diagnosis image. Likewise, the image processor 204 generates a thumbnail image for the touch command screen 104, which will be described later, by reducing a size of the medical image after processing.

Note that the image processor 204 includes an enhancement image processing not shown. In the present embodiment, the image processor 204 performs, as the image processing, enhancement image processing on the generated ultrasonic diagnosis image using multiresolution decomposition processing and nonlinear anisotropic diffusion filter. By the enhancement image processing using the multiresolution decomposition processing and nonlinear anisotropic diffusion filter, the image processor 204 decomposes the ultrasonic diagnosis image with multiresolution, applies nonlinear anisotropic diffusion filter to each decomposed image, and controls a multiresolution high-band signal using an "edge information" generated in the filtering process. The enhancement image processing may perform reduction of an image noise or a speckle, enhancement of an edge of two tissue borders, or coherency enhancement which smooths images around the boundary along a boundary. In other words, the enhancement image processing may independently apply each image quality indicator of the noise reduction, edge enhancement, and coherency enhancement respectively. The image processor 204 may also perform edge detectability, brightness, contrast, and high brightness enhancement as the enhancement image processing. In other words, the enhancement image processing may independently apply each image quality index of edge detectability, brightness, contrast, or high brightness enhancement, respectively. Adjustment methods of each image quality indicator will be described later. Likewise, the image processor 204 may also adjust the image quality of the medical image based on image quality indicators such as a gain or a resolution other than the noise reduction, edge enhancement, coherency enhancement, edge detectability, brightness, contrast, or high brightness enhancement. The coherency enhancement may also be referred to as a smoothness enhancement.

Note that in the present example, although the description, for simplicity, is based on the premise that the enhancement image processing is applied only to images corresponding to an ultrasonic B-mode signal sent from the B-mode processor 202, enhancement image processing may be applied to various images such as color Doppler, contrast imaging, elastography, attenuation imaging, M-mode, or Doppler velocity waveform. Also, the enhancement image processing may be applied to rendered images, MPR images, or 3-dimensional voxel images other than tomograms.

The main display screen 103, in conjunction with the image processor 204, displays the medical image on the screen by converting the image information from the image processor 204 into optical information. In the description of each embodiment below, images output on the main display screen 103 are simply referred to as output images.

The memory 205 stores each information disclosed in the description of the image processor 204 including the B-mode information or the Doppler information. Likewise, the memory 205 also appropriately stores information related to the trajectory as a result of adjusting each image quality indicator, a past trajectory, and an adjustable range of the image quality indicator which will be described later. The memory 205 configures the memory in the present embodiment.

Forms of storing in the memory 205 include a case of temporarily storing a live information and a case of storing in long-term for evidence of the live information acquired. Likewise, the memory 205 also stores a diagnosis information (for example, a patient ID, a doctor opinion etc.) or various data such as a diagnosis protocol or various body marks, etc.

The controller 206 is a processor which realizes functions as an information processing apparatus and controls an overall process of the medical image diagnosis system 100 which is the ultrasonic diagnosis system. The controller 206 is an example of a processing circuitry. Specifically, the controller 206 controls the processing of the transmitter/receiver 201, the B-mode processor 202, the Doppler processor 203, and the image processor 204 based on various setting requirements input by a user via the input apparatus 102, various control programs, and various data. Furthermore, the controller 206 also controls an interface function between the input apparatus 102 and the touch command screen 104.

The input apparatus 102 is connected to the controller 206 and comprises various switches, a button, a trackball, a mouse, and/or a keyboard etc., to introduce various commands from the user, setting commands for a region of interest (ROI), various image quality condition setting commands etc., to the medical image diagnosis system 100.

The touch command screen 104 is an input/output device which comprises both functions as a user input device and as the output device to output information and image to the user. The touch command screen 104, other than outputting user input information to the controller 206, obtains image such as the thumbnail image or graphics necessary for device input from the image processor 204. The touch command screen 104 configures the display in the present embodiment.

The touch command screen 104 may be used together with the trackball, the keyboard, a joystick, the mouse, or one or more similar user input devices known in the art. Likewise, the touch command screen 104 may be used together with other screens such as a non-touch command screen. Likewise, two or more user input devices and/or the output device may be provided. For instance, the touch command screen 104 may be provided together with at least one other input device such as the trackball, the keyboard, the joystick, or the mouse.

Likewise, by modifying the medical image diagnosis system 100 according to the present embodiment, the main display screen 103 and the touch command screen 104 may be on the same device. Furthermore, the main display screen 103, the touch command screen 104, and/or the input apparatus 102 may be separate devices which may be connected to the medical image diagnosis system 100 by a wired or wireless communication.

Likewise, by modifying the medical image diagnosis system 100 according to the present embodiment, the B-mode processor 202, the Doppler processor 203, the image processor 204, the memory 205, and/or the controller 206 may be provided as one function of a server in a location separate from these elements.

Figure 3:
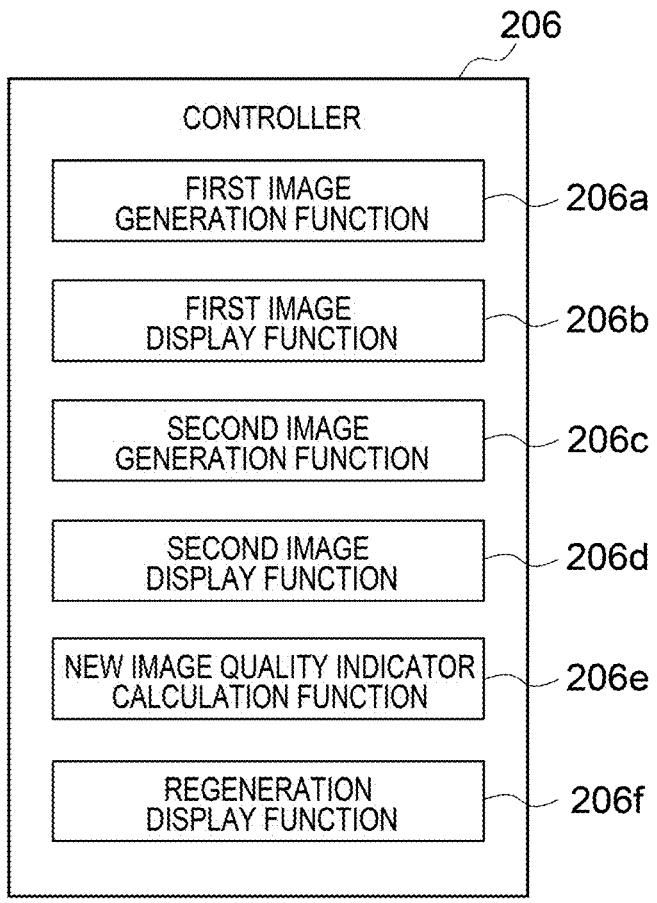
FIG. 3 is a functional block diagram describing functions of a controller of the medical image diagnosis system shown in FIG. 2.

FIG. 3 is a functional block diagram describing functions of the controller 206 of the medical image diagnosis system 100 according to the present embodiment. As shown in FIG. 3, in the present embodiment, the controller 206 comprises a first image generation function 206a, a first image display function 206*b*, a second image generation function 206*c*, a second image display function 206*d*, a new image quality indicator calculating function 206*e*, and a regeneration display function 206*f*. The first image generation function 206*a* is equivalent to a first image generation unit in the present embodiment, the first image display function 206*b* is equivalent to a first image display unit in the present embodiment, the second image generation function 206*c* is equivalent to a second image generation unit in the present embodiment, the second image display unit 206*d* is equivalent to a second image display unit in the present embodiment, the new image quality indicator calculating function 206*e* is equivalent to a new image quality indicator calculating unit in the present embodiment, and the regeneration display function 206*f* is equivalent to a regeneration display unit in the present embodiment.

In the present embodiment, each processing function executed in the first image generation function 206*a*, the first image display function 206*b*, the second image generation function 206*c*, the second image display function 206*d*, the new image quality indicator calculating function 206*e*, and the regeneration display function 206*f* is stored in the memory 205 in a form of a computer executable program. The controller 206 realizes functions corresponding to each program by reading the program from the memory 205 and executing the program. In other words, the controller 206 that has read each program will have each function shown in the controller 206 of FIG. 3. Although it is described in FIG. 3 that the first image generation function 206*a*, the first image display function 206*b*, the second image generation function 206*c*, the second image display function 206*d*, the new image quality indicator calculating function 206*e*, and the regeneration display function 206*f* are realized in a single controller 206, these functions may be realized by combining a plurality of independent processors to configure the controller 206 and executing the program with each processor. Likewise, when the first image generation function 206*a*, the first image display function 206*b*, the second image generation function 206*c*, the second image display function 206*d*, the new image quality indicator calculating function 206*e*, and the regeneration display function 206*f* realizes each function, the image processor 204, the memory 205, the input apparatus 102, the main display screen 103, and the touch command screen 104 are appropriately controlled and used.

<Image Quality Adjustment Setting Screen>

Next, an image quality optimization process realized in the medical image diagnosis system 100 according to the present embodiment will be described. In the medical image diagnosis system 100 according to the present embodiment, the optimal image quality may be easily reached by executing the image quality optimization process.

Figure 4:
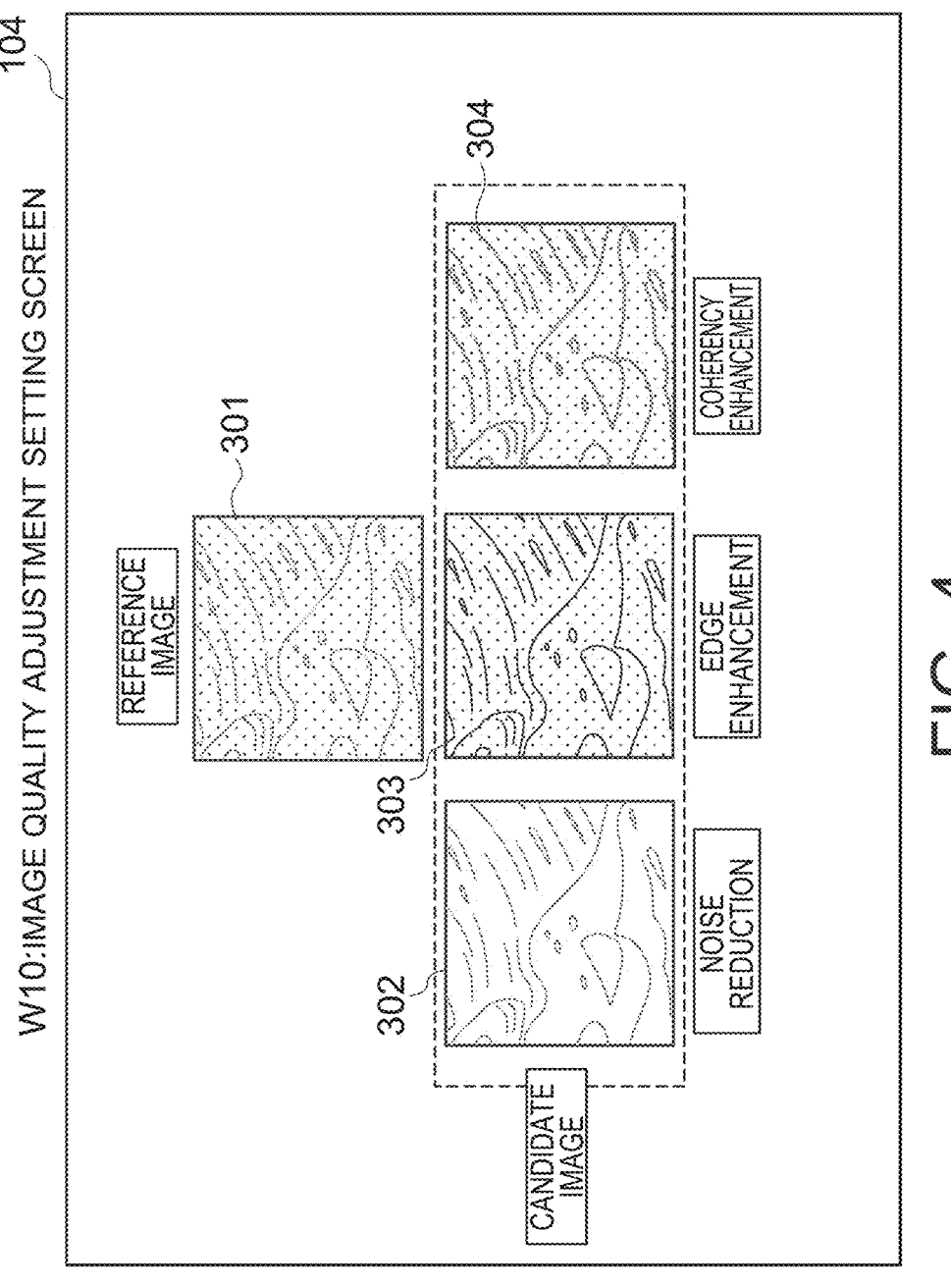
FIG. 4 is a diagram illustrating an exemplary image quality adjustment setting screen displayed on a touch command screen of the medical image diagnosis system according to the first embodiment.

FIG. 4 is a diagram illustrating an exemplary image quality adjustment setting screen W10 displayed on the touch command screen 104 of the medical image diagnosis system 100 according to the present embodiment. In other words, in the medical image diagnosis system 100 according to the present embodiment, although the enhancement image processing is performed in the image processor 204 under a control of the controller 206, the image quality adjustment setting screen W10 is used as a graphical user interface to adjust the image quality.

In the example of FIG. 4, the user may use the image quality adjustment setting screen W10 to perform image quality adjustments of three types of image quality indicators (a noise reduction, an edge enhancement, and a coherency enhancement) by discretely modifying the values of the image quality indicators. Note that image quality indicators which the user may adjust to display the medical image are not limited to these three types, but various image quality indicators may be adjusted. FIG. 4 illustrates a state in which the user has selected three types of image quality indicators (the noise reduction, the edge enhancement, and the coherency enhancement) among the plurality of image quality indicators for adjusting the image quality.

A first to fourth image quality adjustment buttons 301-304 are buttons rendered on the touch command screen 104. In the present embodiment, the first to fourth image quality adjustment buttons 301-304 are configured by the thumbnail images of the medical images. In the thumbnail images, output images of a different plurality of image qualities based on a same medical image data are rendered. The thumbnail image may be a scaled-down version of the output image, or an image where a ROI is set on the output image and only the region of the ROI is cropped out.

Among the first to fourth image quality adjustment buttons 301-304 displayed on the touch command screen 104, on the first image quality adjustment button 301, a thumbnail image that has applied the same image processing as the medical image currently displayed on the main display screen 103 is displayed. This thumbnail image becomes the first image quality adjustment button 301. This is the medical image which becomes a center of the current image quality adjustment, and a group of a value of each image quality indicator to obtain this image quality is referred to as an "anchor" in the present embodiment.

In the example of FIG. 4, since three types of image quality indicators (the noise reduction, the edge enhancement, and the coherency enhancement) are selected as the image quality indicators to adjust, one value of the noise reduction, one value of the edge enhancement, and one value of the coherency enhancement are respectively selected as the anchor. For this reason, the "anchor" may be comprehended as a point defined from values of these image quality indicators. As such, the thumbnail image of the first image quality adjustment button 301 is generated based on the anchor which is the values of the image quality indicators selected by the user. Also, the thumbnail image of the first image quality adjustment button 301 is a reference image for the user to compare and consider the image quality with each thumbnail image of the second to fourth image quality adjustment buttons 302-304. For this reason, the thumbnail image of the first image quality adjustment button 301 may be referred to as the reference image. In the description below, the thumbnail image of the first image quality adjustment button 301 is referred to as the reference image. The reference image is equivalent to a first thumbnail image in the present embodiment.

By operating the image quality adjustment setting screen W10, the user may be increasing or decreasing, from the anchor, each image quality indicator of the noise reduction, the edge enhancement, and the coherency enhancement. The buttons for an operation to increasing or decreasing each image quality indicator are the second to fourth image quality adjustment buttons 302-304. Specifically, the second image quality adjustment button 302 placed leftmost among the second to fourth image quality adjustment buttons 302-304 is a button selected by the user when the value of the image quality indicator of the noise reduction is increased or decreased without changing the value of the other image quality indicators.

Similarly, the third image quality adjustment button 303 placed below the first image quality adjustment button 301 and in the middle of the second to fourth image quality adjustment buttons 302-304 is a button selected by the user when the value of the image quality indicator of the edge enhancement is increased or decreased without changing the other image quality indicators. The fourth image quality adjustment button 304 placed rightmost among the second to fourth image quality adjustment buttons 302-304 is a button selected by the user when the value of the image quality indicator of the coherency enhancement is increased or decreased without changing the other image quality indicators.

The thumbnail images displayed as the second to fourth image quality adjustment buttons 302-304 are thumbnail images generated based on the values of each image quality indicator. Thus, the user may view the thumbnail images displayed as the second to fourth image quality adjustment buttons 302-304 to predict the result of changing the values of the image quality indicators in advance. Then, by this, the values of the image quality indicators may be adjusted more appropriately. Each thumbnail image of the second to fourth image quality adjustment buttons 302-304 is a candidate image to calculate new image quality indicators which will be described below. Thus, each thumbnail image of the second to fourth image quality adjustment buttons 302-304 is referred to as the candidate image. In the description below, the thumbnail images displayed as buttons for an operation to increasing or decreasing each image quality indicator are referred to as candidate images. The candidate image is equivalent to a second thumbnail image in the present embodiment.

After the user views at the reference image and the candidate images displayed on the touch command screen 104 and selects the image quality adjustment button of a most preferable image among the reference and candidate images, the controller 206 calculates the new image quality indicators based on the selected result.

Then, the values of image quality indicators corresponding to the selected one of image quality adjustment button is set as a new anchor, the thumbnail image based on the values of the image quality indicators of the selected one of image quality adjustment button is displayed as the reference image, the image processor 204 performs image processing by using the values of image quality indicators corresponding to the selected one of image quality adjustment button, and the result is displayed as the medical image on the main display screen 103. The controller 206 also generates and displays the candidate image based on the calculated new image quality indicators. As described above, the new image quality indicators are image quality indicators to generate the candidate image displayed on the touch command screen 104 at a step where the user selects a next most preferable image, after the user selects the image quality adjustment button of the most preferable image quality from the reference and candidate images new image quality indicators. In the description below, the new image quality indicators are referred to as image quality indicators for the next step.

In the example shown in FIG. 4, for instance, if the user presses to select the second image quality adjustment button 302, the values the image quality indicators corresponding to the second image quality adjustment button 302 becomes the values of the image quality indicators of the new anchor. As a result, the thumbnail image of the second image quality adjustment button 302 becomes the thumbnail image of the first image quality adjustment button 301. Then, the controller 206 calculates the new image quality indicators based on the selected result of the second image quality adjustment button 302, generates each thumbnail image of the second to fourth image quality adjustment buttons 302-304 based on the calculated new image quality indicators, and displays each generated thumbnail image as the second to fourth image quality adjustment buttons 302-304.

Note that, as described above, for instance, the medical image diagnosis system 100 according to the present embodiment may be configured by an ultrasonic diagnosis system. In view of the real-time nature of the ultrasonic diagnosis system, the image displayed on the main display screen 103 need not be a still image, but rather, the B-mode information sent at a predetermined frame rate from the B-mode processor 202 may be processed in real time by the image processor 204 and displayed on the main display screen 103 as a moving image. Thus, the medical image obtained at the predetermined frame rate may be processed by the image processor 204 in real-time based on the values the image quality indicators of the current anchor selected by the user and displayed on the main display screen as the moving image. In other words, the medical image obtained by the image processor 204 may be image processed based on the values of the image quality indicators corresponding to the reference image, and the moving image in real-time may be displayed on the on the main display screen 103.

As such, when the user presses to select any of the first to fourth image quality adjustment buttons 301-304, the medical image diagnosis system 100 calculates the new image quality indicators based on the selected result of the image quality adjustment buttons, displays the thumbnail image displayed on the selected image quality adjustment button as the first image quality adjustment button 301, and sets the values of the image quality indicators corresponding to the selected one of image quality adjustment button as the new anchor. Then, the medical image diagnosis system 100 generates the candidate image based on the calculated new image quality indicators, displays the generated candidate images as the second to fourth image quality adjustment buttons 302-304, and waits for the user to further press and select the image quality adjustment buttons. By this, since further image quality adjustment becomes possible, new image quality indicators are calculated based on the selected result of the image quality adjustment buttons every time when the image quality adjustment buttons are pressed and selected, and each thumbnail image of the second to fourth image quality adjustment buttons 302-304 are generated based on the calculated new image quality indicators, the user may continuously vary the step width of adjusting the values of the image quality indicators, making it easier to reach the optimal image quality.

When the user reaches a desirable image quality in the image quality adjustment setting screen W10 and wants to end selecting the values of the image quality indicators, the user presses to select an END button (not shown). By this, setting the image quality adjustment of the medical image is ended.

<Image Quality Optimization (Overview of Bayesian Optimization)>

As mentioned above, the medical image diagnosis system 100 calculates the image quality indicators for the next step, i.e., the new image quality indicators based on the selected results of the thumbnail images displayed as each image quality adjustment button. A following method is used to calculate the new image quality indicators.

When calculating the new image quality indicators, a clinical value itself which the user seeks in the medical image is latent in the image quality optimization. Also, the clinical value may be output as statistical observation values, i.e., preference image quality values, by the user selecting images with the highest image quality for the user.

To optimize the image quality, the optimal parameter x* of the processing algorithm that maximizes a quality function $f(x)$ representing the clinical value are to be found. The optimal parameter x* of the processing algorithm that maximizes the quality function $f(x)$ is expressed as in Equation (1).

$$x^* = \arg\max_{x \in \chi \subset \mathbb{R}^d} f(x) \tag{1}$$

Here, d is the dimension, and $\chi \subset \mathbb{R}^d$ is a compact subset. Note that $\chi \subset \mathbb{R}^d$ may possibly include constraints on the parameters.

In the medical image diagnosis system 100 according to the present embodiment, a Bayesian optimization approach, which is an optimization by a probabilistic inference using Bayes' theorem, is adopted to estimate the highest image quality for the user. The Bayesian optimization approach is an approach of optimizing an unknown function based on a posterior distribution of the function by assuming some prior distribution model when deriving an unknown function. An overview of the Bayesian optimization will be described. In the present embodiment, if function $f$ has a probabilistic distribution and a prior distribution model, then the observation values $\mathcal{D}_{1:t}$ including the noise of $f(x_t)$ in sample $x_t$ is expressed as in Equation (2).

$$\mathcal{D}_{1:t} = \{x_{1:t}, f(x_{1:t})\} \tag{2}$$

Also, if the prior distribution is given by $P(\mathcal{D}_{1:t}|f)$, the posterior distribution is obtained as in Equation (3).

$$P(f|\mathcal{D}_{1:t}) \propto P(\mathcal{D}_{1:t}|f)P(f) \tag{3}$$

A commonly assumed prior distribution model of function $f$ is a stochastic process (set of random variables) referred to as a Gaussian process (GP). Thus, in the present embodiment, the prior distribution model of function $f$ is set as the Gaussian process. By using the prior distribution model of function $f$ of the Gaussian process, an acquisition function $\alpha(x)$ that evaluates a utility of candidate points of the next function $f$ is sequentially induced. Then, the next $x_{t+1}$ to explore is selected to maximize $\alpha_t(x)$ leveraging the mean and uncertainty of the posterior distribution $P(f|\mathcal{D}_{1:t})$ for guiding the exploration. As such, the medical image diagnosis system 100 estimates the optimal image quality for the user. The Bayesian optimization will be described in further detail below.

<Image Quality Optimization (Likelihood Model of Image Selection)>

As described above, the touch command screen 104 displays a discrete set of choices of thumbnail images based on the values each image quality indicator. Thus, in the Bayesian optimization approach according to the present embodiment, a Bradley-Terry-Luce (BTL) model is adopted as a likelihood model that allows the user to select the thumbnail image with the image quality preferable to the user from the reference image and the candidate images displayed on the touch command screen 104.

The BTL model is a model applied to observational data based on comparisons between items (e.g., wins and losses between two parties). The probability of choosing item A over item B is expressed by Equation (4) where $\pi_A$ and $\pi_B$ are ratings given to each of item A and item B.

$$P(\text{choose } A \text{ over } B) = P(A \succ B) = \frac{\pi_A}{\pi_A + \pi_B} \tag{4}$$

Note that $\pi = \exp(f_i/s)$ is used. Here, $f_i$ is the quality function to be estimated at point $x_i$ and s is a scale parameter.

The BTL model may also be applied to compare three or more types of items. For example, the probability of selecting A from three types of items A, B, and C is expressed as in Equation (5).

$$P(A \succ \{B, C\}) = \frac{\pi_A}{\pi_A + \pi_B + \pi_C} \tag{5}$$

Note that the BTL model is used as the likelihood model for the discrete choice in the present embodiment, but the likelihood model for discrete choices is not limited to such. For instance, in addition to the BTL model, the Thurstone-Mosteller model is another likelihood model for discrete choice, and the Thurstone-Mosteller model may be applied instead of the BTL model in the present embodiment.

As described above, the Bayesian optimization introduces the assumption that the prior distribution of function $f$ follows the Gaussian process. The Gaussian process is the distribution of functions whose output to input has a normal distribution, and function $f$ is characterized by a mean function m and a covariance function (or kernel) k, as expressed in Equation (6).

$$f(x) \sim \mathcal{GP}(m(x), k(x, x')) \tag{6}$$

The covariance function k represents a similarity between each input point (x and x'). Also, by assuming that there is no prior knowledge of the average function, m(x)=0 is set. On the other hand, the most common method of calculating the covariance function is to use a squared exponential function. The covariance function is expressed as Equation (7).

$$k(x_i, x_j) = \exp\left(-\frac{1}{2}(x_i - x_j)^T \text{diag}(\theta)^{-2}(x - x')\right) \tag{7}$$

Here, $\theta$ is a hyperparameter, a parameter that determines the characteristics of the covariance function.

For this $\theta$ and the observation value of $f$ (preference image quality values $y = y_{1:t}$) at observation samples $x_{1:t}$, a joint Maximum A Posteriori (MAP) estimation applying the Bayes' theorem is performed. The MAP estimation of the preference image quality values y and the hyperparameter $\theta$ is expressed by Equation (8).

$$\left(y^{MAP}, \theta^{MAP}\right) = \arg\max_{(y,\theta)} P(y, \theta|\mathcal{D}) \tag{8}$$

$$= \arg\max_{(y,\theta)} P(\mathcal{D}|y) P(y|\theta) P(\theta)$$

Here, $P(\theta)$ is an arbitrary prior distribution (e.g., lognormal distribution) of the hyperparameter $\theta$.

P($\mathcal{D}$|y) in Equation (8) is calculated using the BTL model described above. The probability that the selection was accumulated is expressed with Equation (9) by applying the BTL model described above to P($\mathcal{D}$|y).

$$P(\mathcal{D}|y) = \prod_t P\left(x_t^{ref} > \{x_t^1, \ldots, x_t^C | y\}\right) \qquad (9)$$

$$= \frac{\pi_2}{\pi_1 + \pi_2} \cdot \frac{\pi_3}{\pi_1 + \pi_2 + \pi_3} \cdots \frac{\pi_k}{\sum_k \pi_k}$$

Here, $$\pi_k = \exp\left(\frac{y_k}{s}\right)$$

is used.

Also, in Equation (8) described above, P(y|θ) is calculated using Equation (10).

$$\log p(y|\theta) = -\frac{1}{2} y^T K_y^{-1} y - \frac{1}{2} \log|K_y| - \frac{n}{2} \log 2\pi \qquad (10)$$

Here, $$K_y = K_f + \sigma_n^2 I$$

is the covariance matrix of the noisy preference image quality y ($K_f$ is the covariance matrix of the noiseless function $f$). As such, θ and y are estimated through applying each Equation described above.

Once θ and y are estimated, the acquisition function α(x) is computed to obtain the next sampling point. The acquisition function α(x) adopts an expected improvement (EI) function in the present embodiment. The EI function is expressed by Equation (11).

$$a^{EI}(x, \mathcal{D}) = E[\max\{0, f(x) - f^+\}] \qquad (11)$$

Here, $f^+$ is the maximum value among the observation data of $f$ as estimated by MAP. The sample point x shown in Equation 11 where the acquisition function becomes maximum is the next sampling point in the Bayesian optimization. As described above, the new image quality indicators are calculated using each Equation described above.

Note that the acquisition function is not limited to the expected improvement function, but may be, for example, each function of an Upper Confidence Bounds (UCB) or Probability of Improvement (PI).

Figure 5:
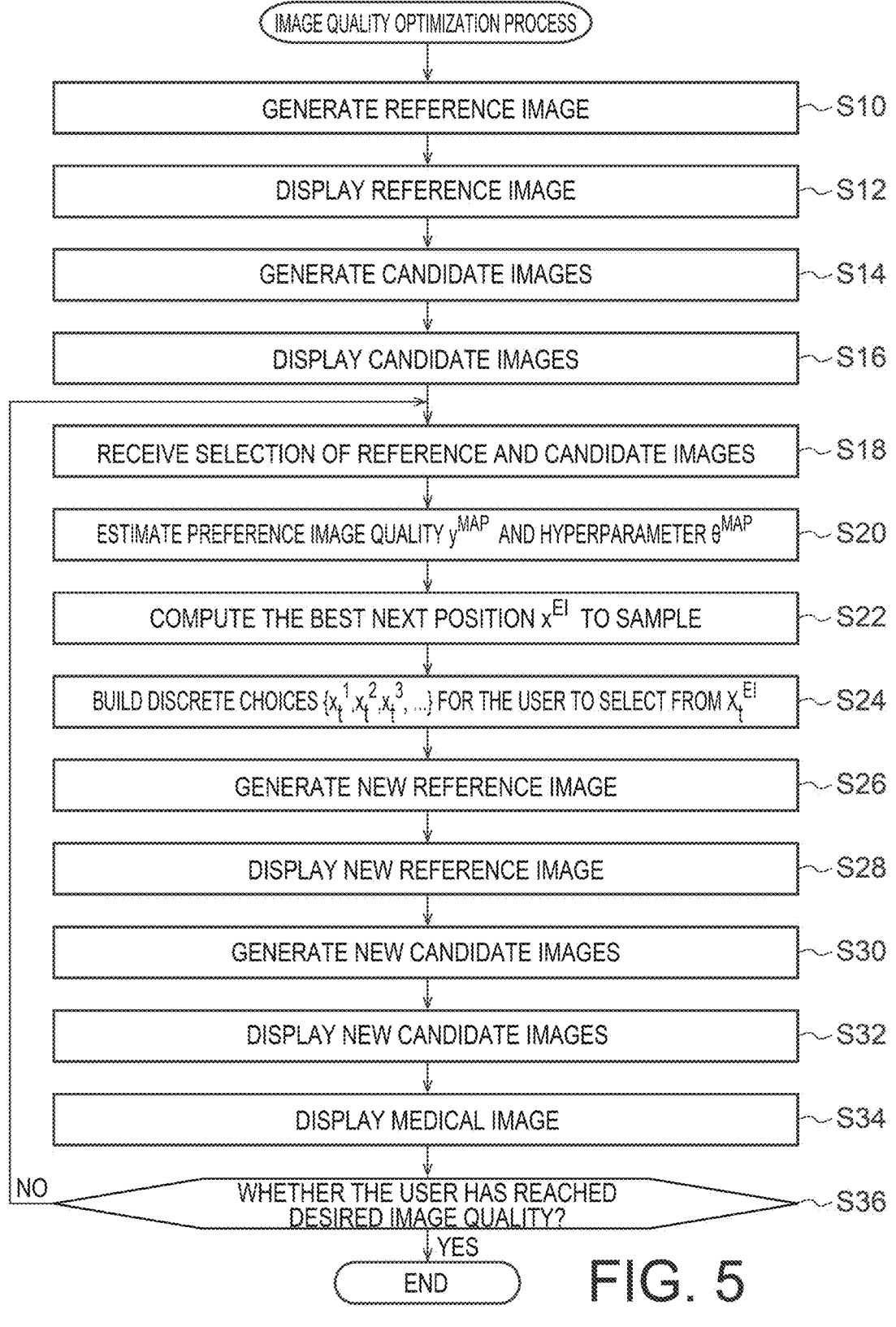
FIG. 5 is a flowchart describing contents of an image quality optimization process executed by the medical image diagnosis system according to the first embodiment.

FIG. 5 is a flowchart describing contents of an image quality optimization process executed by the medical image diagnosis system 100 according to the present embodiment. In other words, the process to set the values of the image quality indicators described using FIG. 4 is realized by the medical image diagnosis system 100 executing the image quality optimization process shown in FIG. 5.

In the present embodiment, the image quality optimization process shown in FIG. 5 is a process executed by the user operating the input apparatus 102 or the touch command screen 104 to command the medical image diagnosis system 100 to initialize the image quality optimization process. In other words, this is the process executed when the user wants to optimize the image quality of the medical image generated hereafter.

As shown in FIG. 5, the medical image diagnosis system 100 first generates the reference image when the image quality optimization process is executed (Step S10). Specifically, the first image generation function 206a in the controller 206 of the medical image diagnosis system 100 controls the image processor 204 to generate the thumbnail image of the first image quality adjustment button 301 as the reference image, based on the values of the image quality indicators of the anchor. At Step S10, the values of the image quality indicators used in the anchor is equal to the values of the image quality indicators of the medical image displayed on the main display screen 103. The controller 206 generates the thumbnail image based on the anchor by controlling and working together with the image processor 204 when generating the thumbnail image of the first image quality adjustment button 301. As described above, the reference image is equivalent to the first thumbnail image in the present embodiment.

Next, as shown in FIG. 5, the medical image diagnosis system 100 displays the reference image generated at Step S10 (Step S12). Specifically, the first image display function 206b in the controller 206 of the medical image diagnosis system 100 displays the thumbnail image based on the values of the image quality indicators of the anchor in the image quality adjustment setting screen W10 of the touch command screen 104 as the first image quality adjustment button 301.

Next, as shown in FIG. 5, the medical image diagnosis system 100 generates the candidate images (Step S14). Specifically, the second image generation function 206c in the controller 206 of the medical image diagnosis system 100 increases (or decreases) the values of the image quality indicators from the anchor, calculates the value of the image quality indicator of each thumbnail image of the second to fourth image quality adjustment buttons 302-304, and generates the thumbnail images of the second to fourth image quality adjustment buttons 302-304 as candidate images based the calculated values of image quality indicators. In the present embodiment, three thumbnail images are to be generated as the candidate images in the image quality adjustment setting screen W10 shown in FIG. 4 described above. Like that of Step S10, these thumbnail images are generated by the controller 206 controlling the image processor 204 and working together with the image processor 204 when generating the thumbnail images around the anchor. As described above, the candidate images are equivalent to the second thumbnail images in the present embodiment.

As shown in FIG. 4 described above, although three sets of the values of image quality indicators to generate each thumbnail image of the second to fourth image quality adjustment buttons 302-304 are to be calculated in the present embodiment, the medical image diagnosis system 100 may calculate two sets of image quality indicators when image quality is adjusted for two types of image quality indicators, or calculate four or more sets of image quality indicators when image quality is adjusted for four or more types of image quality indicators.

Next, as shown in FIG. 5, the medical image diagnosis system 100 displays the candidate images (Step S16). Specifically, the second image display function 206d in the controller 206 of the medical image diagnosis system 100 displays each thumbnail image of the second to fourth image quality adjustment buttons 302-304 generated at Step S14 on the image quality adjustment setting screen W10 of the touch command screen 104. In the image quality adjustment setting screen W10 shown in FIG. 4 described above, three thumbnail images are displayed on the touch command screen 104 as the second to fourth image quality adjustment buttons 302-304. In the present embodiment, as shown in FIG. 4, three thumbnail images are placed side by side below the thumbnail image of the first image quality adjustment button 301 displayed at Step S12. By placing the thumbnail images for which the values of the image quality indicators are modified around the thumbnail image of the anchor, the user may intuitively perceive how the values of image quality indicators should be modified from the current values of the image quality indicators to approach a desired image quality.

Note that, when the medical image diagnosis system 100 displays the thumbnail images of the first to fourth image quality adjustment buttons 301-304, each thumbnail image is assigned with a function of the image quality adjustment buttons corresponding to the values of the image quality indicators of the thumbnail images. In other words, the function of the button that selects the values of image quality indicators of the anchor is assigned to each thumbnail image.

Next, as shown in FIG. 5, the medical image diagnosis system 100 receives a selection of the reference and candidate images (Step S18). Specifically, the new image quality indicator calculating function 206e in the controller 206 of the medical image diagnosis system 100 receives the selection of the reference and candidate images by the user via the input apparatus 102 or the touch command screen 104. In the example shown in FIG. 4, the medical image diagnosis system 100 receives the selection of the first to fourth image quality adjustment buttons 301-304 via the input apparatus 102 or the touch command screen 104.

Next, as shown in FIG. 5, the medical image diagnosis system 100 estimates the preference image quality $y^{MAP}$ and hyperparameter $\theta^{MAP}$ (Step S20). Specifically, the new image quality indicator calculating function 206e in the controller 206 of the medical image diagnosis system 100 estimates the preference image quality $y^{MAP}$ and hyperparameter $\theta^{MAP}$ from the past $(t-1)$ observation value $\mathcal{D}_{1:t-1}$ (sample points and operator's choice).

Next, as shown in FIG. 5, the medical image diagnosis system 100 computes a best next position $x^{EI}$ to sample (Step S22). Specifically, the new image quality indicator calculating function 206e in the controller 206 of the medical image diagnosis system 100 computes the next sampling position $x^{EI}$ by maximizing the acquisition function (EI).

Next, as shown in FIG. 5, the medical image diagnosis system 100 builds discrete choices $$\{x_t^1, x_t^2, x_t^3, \dots\}$$

for the user to select from $$x_t^{EI}$$

(Step S24). Specifically, the new image quality indicator calculating function 206e in the controller 206 of the medical image diagnosis system 100 builds the set of the values of the image quality indicators as discrete choices for the user to select from $$x_t^{EI}.$$

In the present embodiment, the new image quality indicator calculating function 206e builds $\{N_t, E_t, C_t\}$ as discrete choices, consisting of noise reduction $N_t$, edge enhancement $E_t$, and coherency enhancement $C_t$.

Next, as shown in FIG. 5, the medical image diagnosis system 100 generates a new reference image (Step S26). Specifically, the regeneration display function 206f in the controller 206 of the medical image diagnosis system 100 sets the values of the image quality indicators corresponding to the thumbnail image of the image quality adjustment button selected by the user among the thumbnail images of the image quality adjustment buttons displayed on the touch command screen 104 at Step S18. Then, the regeneration display function 206f causes the first image generation function 206a to generate the reference image based on the values of the image quality indicators of the new anchor. More specifically, the first image generation function 206a generates the thumbnail image of the first image quality adjustment button 301 as the new reference image based on the image quality indicators $\{N_{t-1}, E_{t-1}, C_{t-1}\}$ before change, which is the new anchor. Like Step S10, the controller 206 generates the thumbnail image based on the new anchor by controlling and working together with the image processor 204.

Next, as shown in FIG. 5, the medical image diagnosis system 100 displays the new reference image (Step S28). Specifically, the regeneration display function 206f in the controller 206 of the medical image diagnosis system 100 causes the first image display function 260b to display the new thumbnail image based on the values of the image quality indicators of the new anchor generated at Step S26 on the image quality adjustment setting screen W10 of the touch command screen 104 as the first image quality adjustment button 301.

Next, as shown in FIG. 5, the medical image diagnosis system 100 generates new candidate images (Step S30). Specifically, the regeneration display function 206f in the controller 206 of the medical image diagnosis system 100 causes the second image generation function 206c to generate the new thumbnail images of the second to fourth image quality adjustment buttons 302-304 as new candidate images based on the set of the values of image quality indicators built by the new image quality indicator calculating function 206e at Step S24.

In the present embodiment, three thumbnail images are to be generated on the image quality adjustment setting screen W10 shown in FIG. 4 described above. The thumbnail image corresponding to the second image quality adjustment button 302 among the three thumbnail images modifies only the image quality indicator of noise reduction from the image quality indicators $\{N_{t-1}, E_{t-1}, C_{t-1}\}$ of the new anchor. In other words, the values of the image quality indicators of the thumbnail image corresponding to the second image quality adjustment button 302 becomes $\{N_{t-1}, E_{t-1}, C_{t-1}\}$. Also, the thumbnail image corresponding to the third image quality adjustment button 303 among the three thumbnail images modifies only the image quality indicator of edge enhancement from the image quality indicators $\{N_{t-1}, E_{t-1}, C_{t-1}\}$ of the new anchor. In other words, the values of the image quality indicators of the thumbnail image corresponding to the third image quality adjustment button 303 becomes $\{N_{t-1}, E_{t-1}, C_{t-1}\}$. Also, the thumbnail image corresponding to the fourth image quality adjustment button 304 among the three thumbnail images modifies only the image quality indicator of coherency enhancement from the image quality indicators $\{N_{t-1}, E_{t-1}, C_{t-1}\}$ of the new anchor. In other words, the values of the image quality indicators of the thumbnail image corresponding to the fourth image quality adjustment button 304 becomes $\{N_{t-1}, E_{t-1}, C_{t-1}\}$.

Note that, like Step S10, when generating the thumbnail images around the anchor, these thumbnail images are generated by the controller 206 controlling the image processor 204 and working together with the image processor 204. As described above, the thumbnail images of the second to fourth image quality adjustment buttons 302-304 are equivalent to the second thumbnail image in the present embodiment.

Next, as shown in FIG. 5, the medical image diagnosis system 100 displays new candidate images (Step S32). Specifically, the regeneration display function 206f in the controller 206 of the medical image diagnosis system 100 cause the second image display function 206d to display each thumbnail image of the second to fourth image quality adjustment buttons 302-304 generated at Step S30 as new candidate images on the image quality adjustment setting screen W10 of the touch command screen 104.

Note that, when the medical image diagnosis system 100 displays the thumbnail images of the first to fourth image quality adjustment buttons 301-304, each thumbnail image is assigned with the function of the image quality adjustment buttons corresponding to the values of the image quality indicators of the thumbnail images. In other words, the function of the button that selects the values of the image quality indicators of the anchor is assigned to each thumbnail image.

Next, as shown in FIG. 5, the medical image diagnosis system 100 displays the medical image applied with the values of the image quality indicators of the selected image quality adjustment button (Step S34). Specifically, the regeneration display function 206f in the controller 206 of the medical image diagnosis system 100 displays the medical image applied with the values of image quality indicators of the image quality adjustment button selected by the user at Step S18 on the main display screen 103. In other words, the medical image diagnosis system 100 generates the new medical image using the same values of the image quality indicators as the values of image quality indicators used when generating the thumbnail image of the first image quality adjustment button 301 and displays the generated medical image on the main display screen 103.

Next, as shown in FIG. 5, the medical image diagnosis system 100 judges whether the user has reached a desired image quality (Step S36). Specifically, the regeneration display function 206f in the controller 206 of the medical image diagnosis system 100 judges whether the user has reached the desired image quality by whether the END button (not shown) or a continue button (not shown) has been selected.

Then, when judging that the user has not reached the desired image quality by the user pressing the continue button (Step S36: No), the medical image diagnosis system 100 returns to Step S18 and repeats the process from Steps S18 to S36 until the user reaches the desired image quality. In the present embodiment, although the medical image diagnosis system 100 determines that the user has not reached the desired image quality by the user pressing the continue button, the medical image diagnosis system 100 may determine that the user has not reached the desirable image quality by the user pressing the image quality adjustment buttons displayed at Steps S28 to S32 instead of the continue button.

On the other hand, when judging that the user has reached the desired image quality by the user pressing the END button (Step S36: Yes), the image quality optimization process according to the present embodiment ends. By this, the medical image displayed on the main display screen 103 becomes an image with a high clinical value for the user.

As described above, in the medical image diagnosis system 100 according to the present embodiment, since, by executing the image quality optimization process, each value of an image quality indicator difference $\{\Delta N, \Delta E, \Delta C\}$ between the values of the image quality indicators $\{N_{t-1}, E_{t-1}, C_{t-1}\}$ before change and the values of the image quality indicators $\{N_t, E_t, C_t\}$ after change are computed every time the selection of the image quality adjustment buttons is received, the step width of adjusting the values of the image quality indicators becomes variable, making it easier to reach the desired image quality. In other words, it becomes easier for the user to adjust the image quality of medical images according to the medical image diagnosis system 100 of the present embodiment.

Note that, in reality, the image processing in the image processor 204 of the medical image diagnosis system 100 described above often involves a plurality of parameters. In that case, it is necessary to convert the values of the image quality indicators selected by the user into parameters used in the image processor 204 by calculation. By converting the values of the image quality indicators into parameters as such, the values of the image quality indicators selected by the user may be indirectly used to adjust the image quality of the medical image.

For instance, when, in three types of image quality indicators of noise reduction N, edge enhancement E, and coherency enhancement C, defining the image quality indicators as $S=\{N, E, C\}$ and the parameters as $P=\{p_1, p_2, \ldots, p_n\}$, the conversion by calculation may be expressed by an Equation $P=F(S)$. If this function is linear, F may be expressed as a matrix with the equation $P=FS$.

Thus, in the image quality optimization process of FIG. 5 described above, the first image generation function 206a of the controller 206 at Step S10, the second image generation function 206c of the controller 206 at Step S14, and the new image quality indicator calculating function 206e at Step S22 may calculate the plurality of parameters from the values of the image quality indicators selected by the user, and control the image processor 204 to generate various thumbnail images based on the calculated parameters. Otherwise, the first image generation function 206a of the controller 206 at Step S10, the second image generation function 206c of the controller 206 at Step S14, and the new image quality indicator calculating function 206e at Step S22 may output the values of the image quality indicators selected by the user to the image processor 204, and the image processor 204 may calculate the plurality of parameters from the values of the image quality indicators and generate various thumbnail images based on these calculated parameters.

First Modification

In the first embodiment described above, it was impossible to select increasing or decreasing the values of the image quality indicators for the next step since each value of the image quality indicator for the next step are calculated based on the selected result of the thumbnail images displayed in each image quality adjustment button, but modifications may be made to allow the user to select increasing or decreasing the values of the image quality indicators for the next step. Parts that differ from that of the first embodiment described above will be described below as a first modification applied to the first embodiment.

Figure 6:
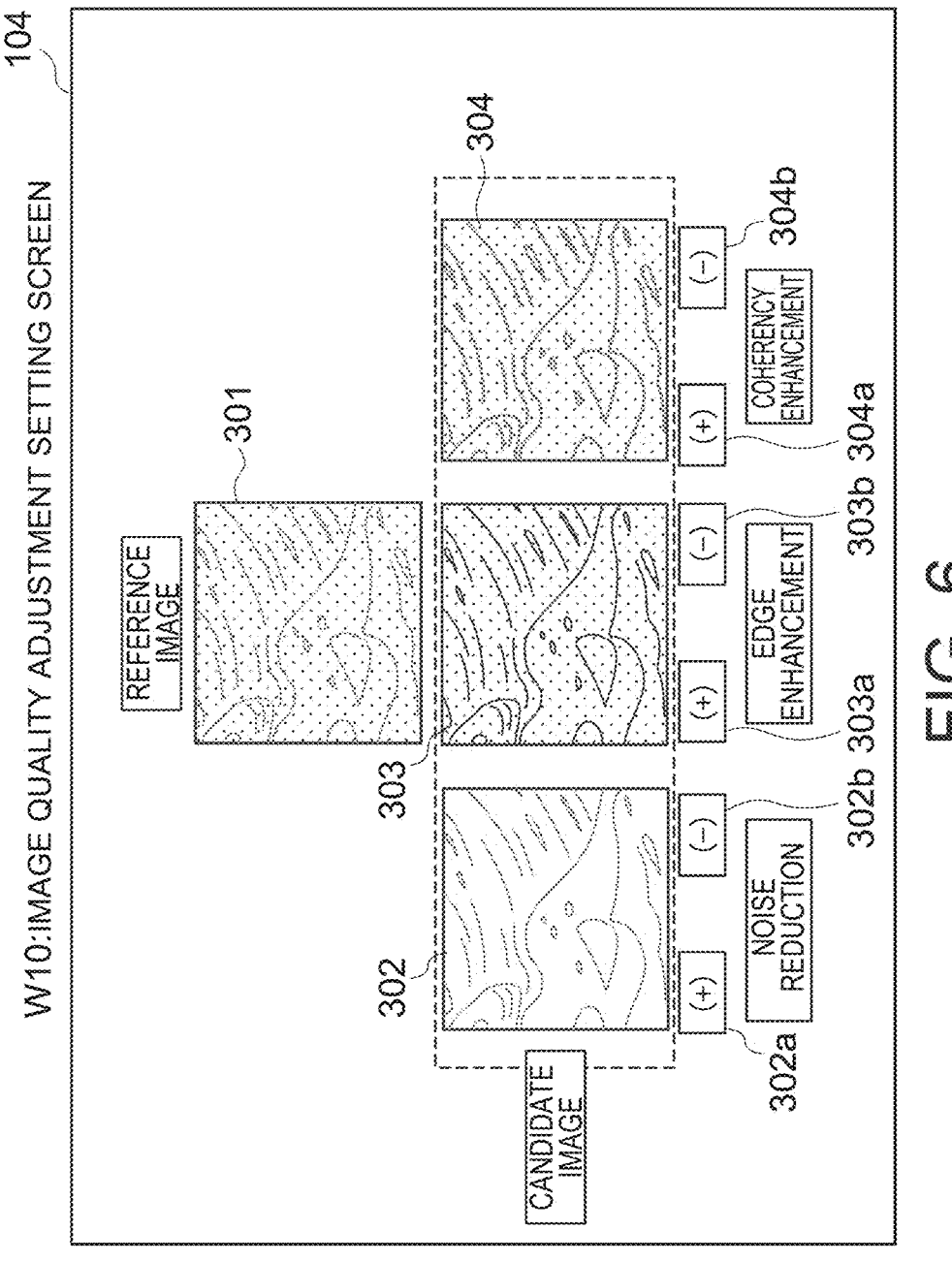
FIG. 6 is a diagram illustrating the exemplary image quality adjustment setting screen displayed on the touch command screen of the medical image diagnosis system according to a first modification.

FIG. 6 is a diagram illustrating the exemplary image quality adjustment setting screen W10 displayed on the touch command screen 104 of the medical image diagnosis system 100 according to the first modification, which corresponds to FIG. 4 described above. As shown in FIG. 6, switching buttons 302a, 302b, 303a, 303b, 304a, and 304b to switch increasing and decreasing the image quality indicators for the next step are respectively displayed below the second to fourth image quality adjustment buttons 302-304 on the image quality adjustment setting screen W10 according to the present modification.

For instance, if the user presses to select the second image quality adjustment button 302 after pressing the switching button 302a, the new image quality indicator calculating function 206e in the controller 206 of the medical image diagnosis system 100 calculates the image quality indicator of noise reduction $\{N_t\}$ such that the image quality indicator of noise reduction $\{N_t\}$ for the next step is increased with respect to the image quality indicator of noise reduction for the new anchor $\{N_{t-1}\}$. On the other hand, if the user presses to select the second image quality adjustment button 302 after pressing the switching button 302b, the new image quality indicator calculating function 206e in the controller 206 of the medical image diagnosis system 100 calculates the image quality indicator of noise reduction $\{N_t\}$ such that the image quality indicator of noise reduction $\{N_t\}$ for the next step is decreased with respect to the image quality indicator of noise reduction for the new anchor $\{N_{t-1}\}$.

Similarly, in the present embodiment, the switching buttons 303a, 303b are buttons to switch increasing and decreasing the image quality indicator of edge enhancement for the next step $\{E_t\}$ with respect to the image quality indicator of edge enhancement for the new anchor $\{E_{t-1}\}$. Further, the switching buttons 304a, 304b are buttons to switch increasing and decreasing the image quality indicator of coherency enhancement for the next step $\{C_t\}$ with respect to the image quality indicator of coherency enhancement for the new anchor $\{C_{t-1}\}$.

As described above, in the medical image diagnosis system 100 according to the first modification of the present embodiment, since it is possible to switch increasing and decreasing the image quality indicators for the next step with respect to the image quality indicators for the new anchor based on the user operation by operating the switching buttons, the user may predict the result of changing the image quality indicator values in advance and avoid unintentional changes.

Second Embodiment

Although the example related to the image quality adjustment setting screen W10 displayed on the touch command screen 104 was described in the medical image diagnosis system 100 according to the first embodiment described above, there are modifications other than the described example where the interface is modified. For instance, in the medical image diagnosis system 100 according to the first embodiment described above, the medical image where one type of image quality indicator is modified may be confirmed as the thumbnail image, but the medical image where two or more types of image quality indicators are simultaneously modified cannot be confirmed. Thus, in a second embodiment, in addition to an example of the thumbnail image where one type of image quality indicator is modified, an example of a composed image where the plurality of image quality indicators is simultaneously modified in a single screen displayed on the touch command screen 104 will be described. Parts that differ from that of the first embodiment described above will be described.

Figure 7:
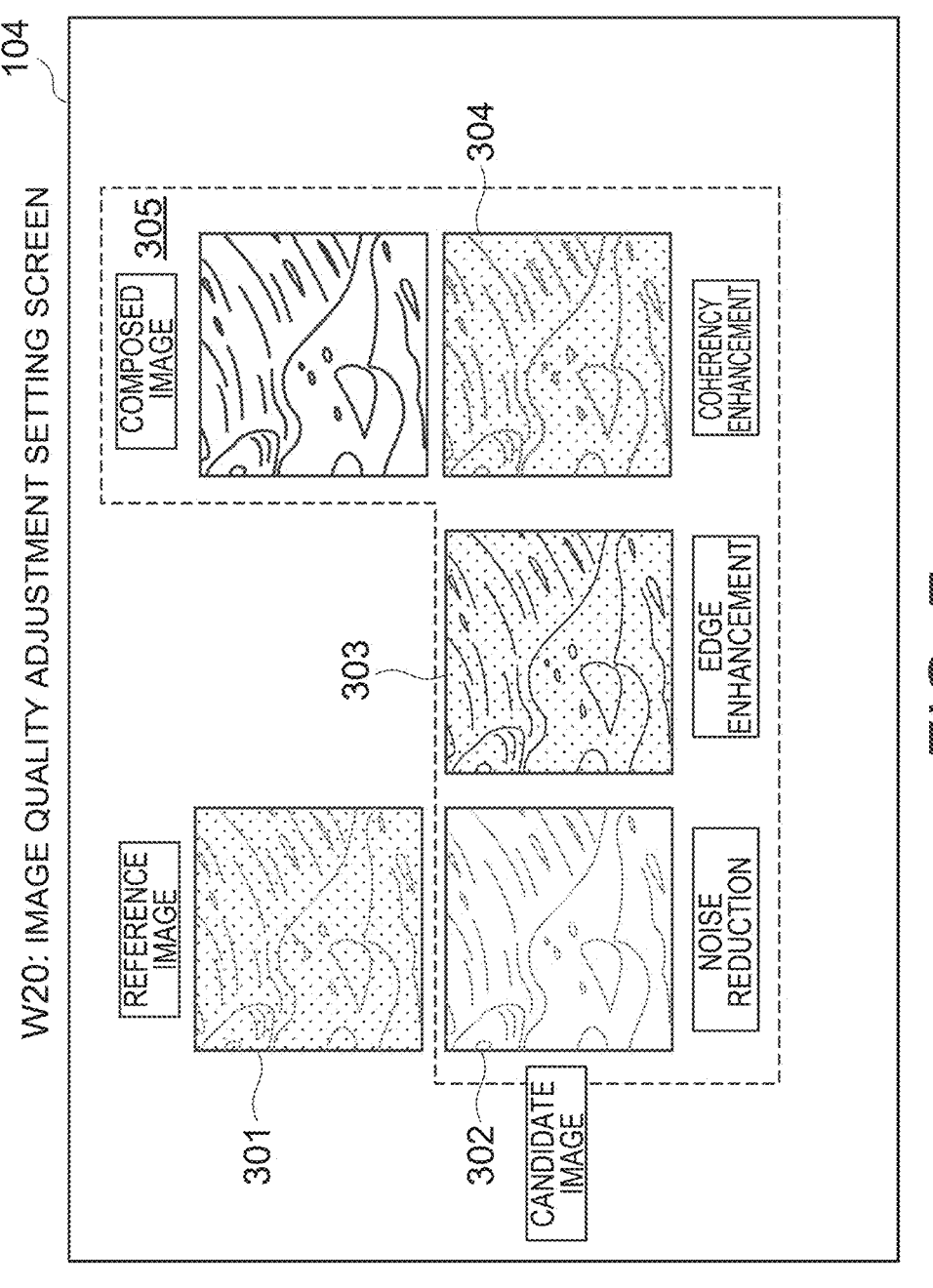
FIG. 7 is a diagram illustrating the exemplary image quality adjustment setting screen displayed on the touch command screen of the medical image diagnosis system according to a second embodiment.

FIG. 7 is a diagram illustrating the exemplary image quality adjustment setting screen W20 displayed on the touch command screen 104 of the medical image diagnosis system 100 according to the second embodiment, which corresponds to FIG. 4 in the first embodiment described above. As shown in FIG. 7, the image quality adjustment setting screen W20 according to the present embodiment allows to adjust all three types of image quality indicator values (the noise reduction, the edge enhancement, and the coherency enhancement) on a single screen, in addition to adjusting each value of the image quality indicator of the noise reduction, the edge enhancement, and the coherency enhancement. In other words, a fifth image quality adjustment button 305 to adjust all three types of the values of the image quality indicators of the noise reduction, the edge enhancement, and the coherency enhancement is added in the image quality adjustment setting screen W20 according to the present embodiment, in addition to the image quality adjustment buttons to adjust each value of the image quality indicator of noise reduction, edge enhancement, and coherency enhancement. As such, four image quality adjustment buttons to adjust the image quality for three image quality indicators (the noise reduction, the edge enhancement, and the coherency enhancement) are displayed on the image quality adjustment setting screen W20 according to the present embodiment. In other words, the number of the thumbnail images corresponding to the image quality adjustment buttons to adjust the image quality displayed on the image quality adjustment setting screen W20 according to the present embodiment is greater than the number of types of the image quality indicators.

Also, as shown in FIG. 7, the first image quality adjustment button 301 is located above the second image quality adjustment button 302, and the second to fourth image quality adjustment buttons 302-304 are located below the first image quality adjustment button 301 in order from left to right, and the fifth image quality adjustment button 305 is located above the fourth image quality adjustment button 304 in the image quality adjustment setting screen W20 according to the present embodiment.

Figure 8:
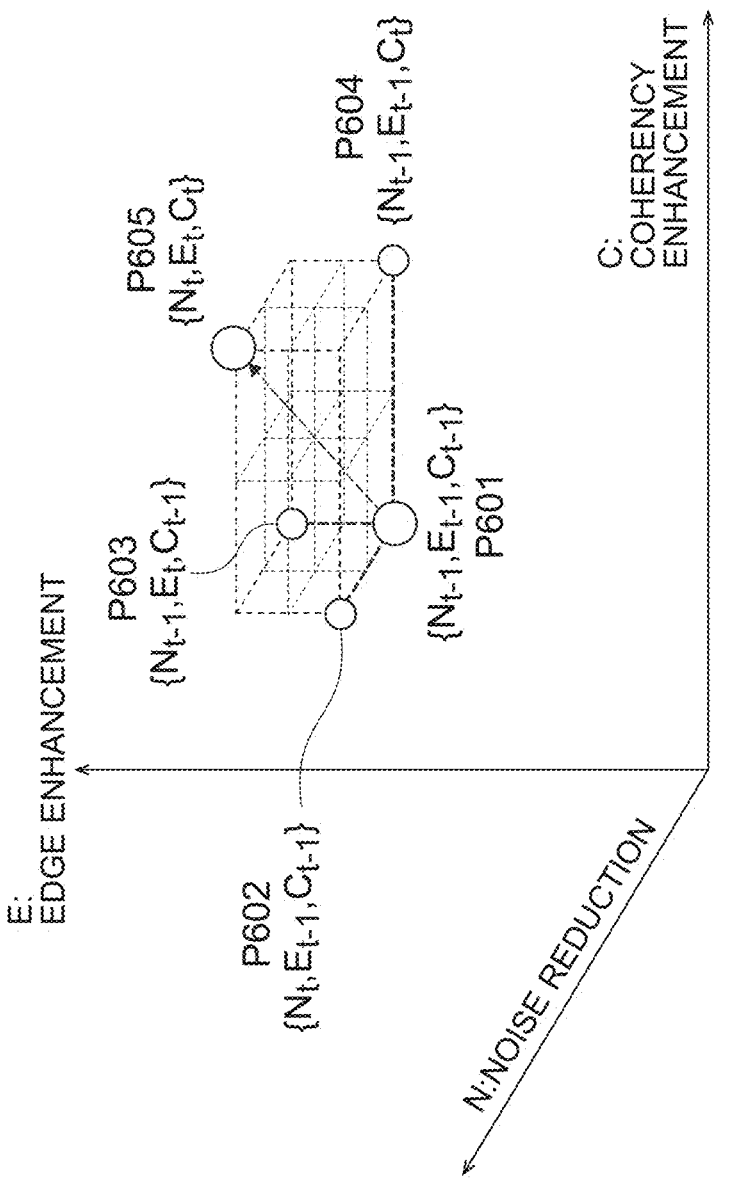
FIG. 8 is a diagram illustrating a change of an image quality indicator in 3-dimensional coordinates in the medical image diagnosis system according to the second embodiment.

FIG. 8 is a diagram illustrating the change of image quality indicators in 3-dimention coordinates in the medical image diagnosis system 100 according to the second embodiment. An origin represents the values of the image quality indicators $\{N_0, E_0, C_0\}$ of the thumbnail image of the first image quality adjustment button 301 at the start of the image quality optimization process, an X-axis represents the value of the coherency enhancement C, a Y-axis represents the value of the noise reduction N, and a Z-axis represents the value of the edge enhancement E. In FIG. 8, a state is shown where the image quality adjustment buttons are operated t times, i.e., where Bayesian optimization is performed t times.

Point P601 shows the values of the image quality indicators when generating the thumbnail image of the first image quality adjustment button 301. In other words, in the example shown in FIG. 8, point P601 shows the values of the image quality indicator $\{N_{t-1}, E_{t-1}, C_{t-1}\}$ of the thumbnail image of the image quality adjustment button selected by the user's (t−1) times of operation of the image quality adjustment button.

Point P602 shows the values of the image quality indicators when generating the thumbnail image of the second image quality adjustment button 302, which is the candidate image to adjust the noise reduction. In other words, in the example shown in FIG. 8, point P602 shows the values of the image quality indicators $\{N_t, E_{t-1}, C_{t-1}\}$ where only the value of image quality indicator of noise reduction is modified, calculated by computing t times of Bayesian optimization to the values of the image quality indicators of the thumbnail image of the first image quality adjustment button 301.

Point P603 shows the values of the image quality indicators when generating the thumbnail image of the thumbnail image of the third image quality adjustment button 303, which is the candidate image to adjust the edge enhancement. In other words, in the example shown in FIG. 8, point P603 shows the values of the image quality indicators $\{N_{t-1}, E_t, C_{t-1}\}$ where only the value of image quality indicator of edge enhancement is modified, calculated by computing t times of Bayesian optimization to the values of the image quality indicators of the thumbnail image of the first image quality adjustment button 301.

Point P604 shows the values of the image quality indicators when generating the thumbnail image of the thumbnail image of the fourth image quality adjustment button 304, which is the candidate image to adjust the coherency enhancement. In other words, in the example shown in FIG. 8, point P604 shows the values of image quality indicators $\{N_{t-1}, E_{t-1}, C_t\}$ where only the value of image quality indicator of coherency enhancement is modified, calculated by computing t times of Bayesian optimization to the values of the image quality indicators of the thumbnail image of the first image quality adjustment button 301.

Point P605 shows the values of image quality indicator when generating the composed image of the fifth image quality adjustment button 305 to adjust all three types of the values of the image quality indicators (the noise reduction, the edge enhancement, and the coherency enhancement). In other words, in the example shown in FIG. 8, point P605 shows the values of the image quality indicators $\{N_t, E_t\}$, $$x_t^{EI}$$

where all three types of the values of the image quality indicators (the noise reduction, the edge enhancement, and the coherency enhancement) are modified, calculated by computing t times of Bayesian optimization to the values of the image quality indicators of the thumbnail image of the first image quality adjustment button 301.

As described above, in the medical image diagnosis system 100 according to the present embodiment, since all three types of the values of the image quality indicators (the noise reduction, the edge enhancement, and the coherency enhancement) may be adjusted on a single screen in addition to adjusting each value of the image quality indicator of the noise reduction, the edge enhancement, and the coherency enhancement, the user may easily adjust the image quality of the medical image.

Second Modification

In the second embodiment described above, it was impossible to select increasing or decreasing the values of the image quality indicators for the next step, since each value of the image quality indicator for the next step is calculated based on the selected result of the thumbnail image displayed on each image quality adjustment button, but modifications that allow the user to select increasing or decreasing the values of the image quality indicators for the next step are possible. Parts that differ from that of the second embodiment described above will be described as a second modification applied to the second embodiment.

Figure 9:
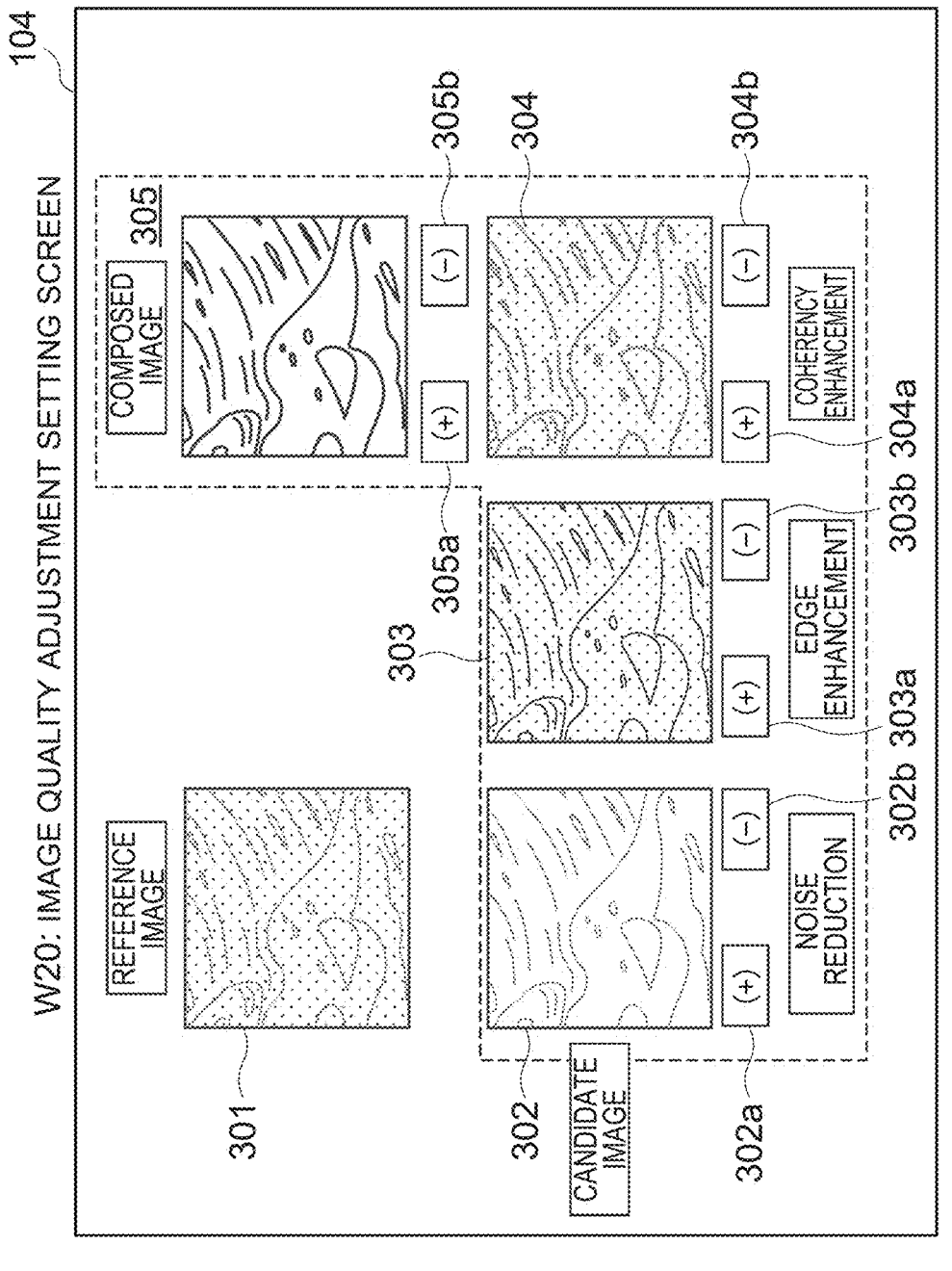
FIG. 9 is a diagram illustrating the exemplary image quality adjustment setting screen displayed on the touch command screen of the medical image diagnosis system according to a second modification.

FIG. 9 is a diagram illustrating the exemplary image quality adjustment setting screen W20 displayed on the touch command screen 104 of the medical image diagnosis system 100 according to the second modification, which corresponds to FIG. 7 described above. As shown in FIG. 9, the switching buttons 302a, 302b, 303a, 303b, 304a, 304b, 305a, and 305b to switch increasing and decreasing the image quality indicators for the next step are displayed below each of the second to fifth image quality adjustment buttons 302-305 on the image quality adjustment setting screen W20 according to the present modification. Description will be omitted for the switching buttons 302a, 302b, 303a, 303b, 304a, and 304b which is equivalent to those of the first modification of the first embodiment described above.

If the user presses to select the fifth image quality adjustment button 305 after pressing the switching button 305a, the new image quality indicator calculating function 206e in the controller 206 of the medical image diagnosis system 100 calculates the image quality indicators of the noise reduction, the edge enhancement, and the coherency enhancement $\{N_t, E_t, C_t\}$ such that the image quality indicators of the noise reduction, the edge enhancement, and the coherency enhancement for the next step $\{N_t, E_t, C_t\}$ is increased with respect to the image quality indicator of the noise reduction, the edge enhancement, and the coherency enhancement for the new anchor $\{N_{t-1}, E_{t-1}, C_{t-1}\}$. On the other hand, if the user presses to select the second image quality adjustment button 305 after pressing the switching button 305b, the new image quality indicator calculating function 206e in the controller 206 of the medical image diagnosis system 100 calculates the image quality indicators of the noise reduction, the edge enhancement, and the coherency enhancement $\{N_t, E_t, C_t\}$ such that the image quality indicators of the noise reduction, the edge enhancement, and the coherency enhancement for the next step $\{N_t, E_t, C_t\}$ is decreased with respect to the image quality indicators of the noise reduction, the edge enhancement, and the coherency enhancement for the new anchor $\{N_{t-1}, E_{t-1}, C_{t-1}\}$. In other words, the switching buttons 305a, 305b are buttons to switch increasing and decreasing the image quality indicators of the noise reduction, the edge enhancement, and the coherency enhancement for the next step $\{N_t, E_t, C_t\}$ with respect to the image quality indicators of the noise reduction, the edge enhancement, and the coherency enhancement for the new anchor $\{N_{t-1}, E_{t-1}, C_{t-1}\}$.

As described above, since it is possible to switch increasing and decreasing the image quality indicators for the next step with respect to the image quality indicators for the new anchor based on the user operation by operating the switching buttons in the medical image diagnosis system 100 according to the second modification, the user may predict the result of changing the image quality indicator values in advance and avoid unintentional changes.

Third Embodiment

In the first and second embodiments described above, three types of image quality indicators (the noise reduction, the edge enhancement, and the coherency enhancement) were adjusted on a single screen, but four types of image quality indicators may be adjusted on a single screen. Thus, in a third embodiment, an example where four types of image quality indicators are adjusted on a single screen displayed on the touch command screen will be described. Parts that differ from that of the first embodiment described above will be described.

Figure 10:
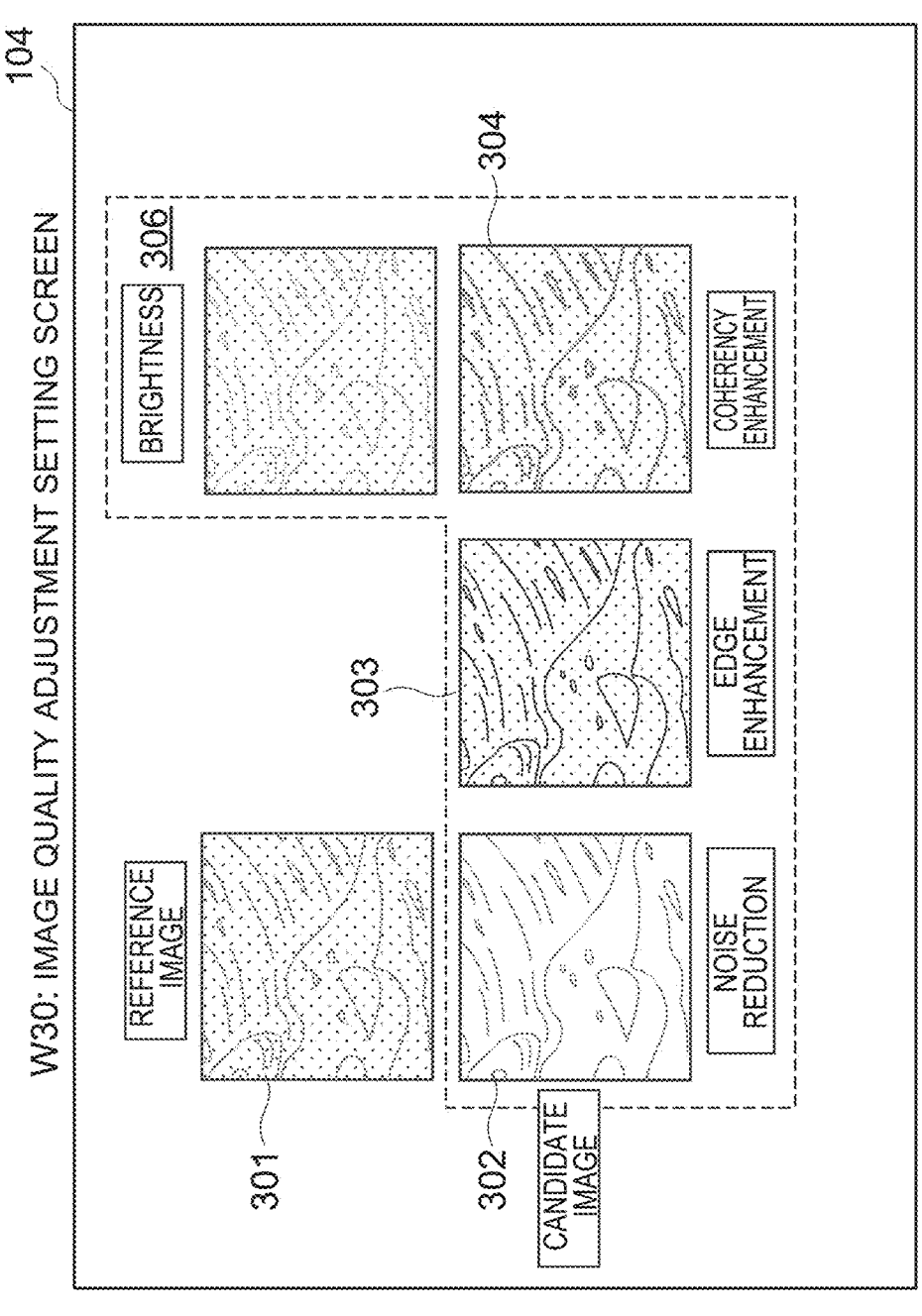
FIG. 10 is a diagram illustrating the exemplary image quality adjustment setting screen displayed on the touch command screen of the medical image diagnosis system according to a third embodiment.

FIG. 10 is a diagram illustrating the exemplary image quality adjustment setting screen W30 displayed on the touch command screen 104 of the medical image diagnosis system 100 according to the third embodiment, which corresponds to FIG. 4 of the first embodiment described above. As shown in FIG. 10, a sixth image quality adjustment button 306 to adjust the values of the image quality indicators of brightness is added to the image quality adjustment setting screen W30 according to the present embodiment, in addition to the image quality adjustment buttons to adjust each of the three types of the values of the image quality indicators (the noise reduction, the edge enhancement, and the coherency enhancement).

The sixth image quality adjustment button 306 may be selected by the user to increasing or decreasing the values of the image quality indicators of brightness without modifying the other image quality indicators. In the example shown in FIG. 10, the sixth image quality adjustment button 306 may be placed above the fourth image quality adjustment button 304.

As described above, since the image quality adjustment buttons to adjust each of the four types of image quality indicators may be displayed on the touch command screen 104 in the medical image diagnosis system 100 according to the present embodiment, four types of image quality indicators may be adjusted on a single screen, allowing to adjust multiple image quality indicators at once and making it easier for the user to adjust the image quality of the medical image.

Note that, four types of image quality indicators are allowed to be adjusted on a single screen in the third embodiment described above, but five or more image quality indicators may be adjusted on a single screen if the touch command screen 104 allows its display. Likewise, if five or more image quality indicators cannot be displayed on a single screen, the user is to operate the touch command screen 104 and select which image quality indicators to display and adjust on a single screen among the plurality of image quality indicators. For instance, if there are 10 types of image quality indicators which the user may adjust, the user is to select four types among those.

Third Modification

In the first to third embodiments described above, the image quality adjustment setting screens W10, W20, and W30 may be modified to display the images at the start of image quality adjustment to confirm the change of image quality from the images at the start of image quality adjustment in each thumbnail image of the first to sixth image quality adjustment buttons 301-306. Parts that differ from that of the second embodiment described above will be described as a third modification applied to the second embodiment.

Figure 11:
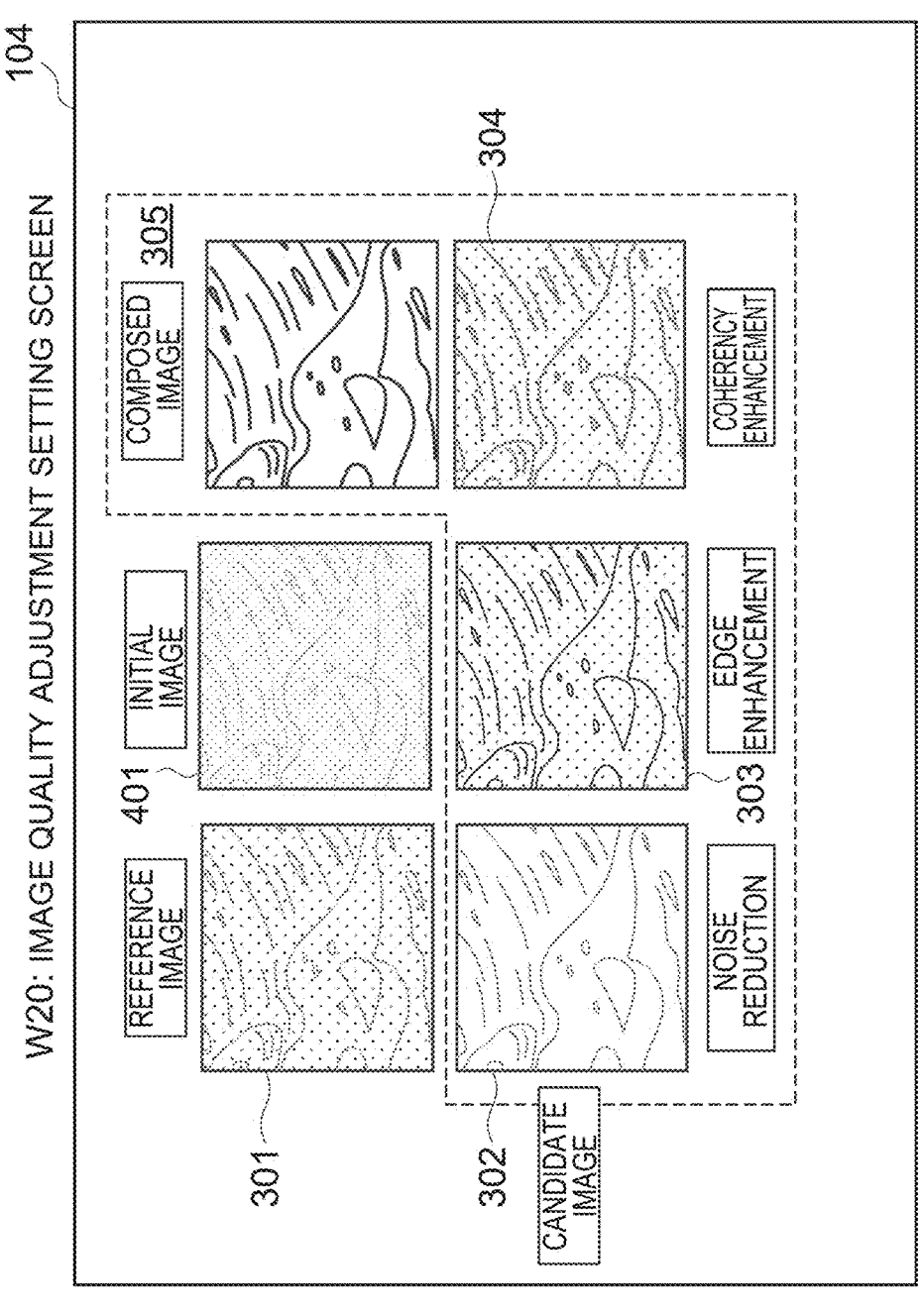
FIG. 11 is a diagram illustrating the exemplary image quality adjustment setting screen displayed on the touch command screen of the medical image diagnosis system according to a third modification.

FIG. 11 is a diagram illustrating the exemplary image quality adjustment setting screen W20 displayed on the touch command screen 104 of the medical image diagnosis system 100 according to the third modification, which corresponds to FIG. 7 described above. As shown in FIG. 11, the thumbnail image 401 is displayed on the image quality adjustment setting screen W20 according to the third modification, in addition to the first to fifth image quality adjustment buttons 301-305.

The thumbnail image 401 is an image at the start of image quality adjustment. In other words, it is the image applied with the values of the image quality indicators of the thumbnail image of the first image quality adjustment button 301 generated at Step S10 of the image quality optimization process described above. The thumbnail image 401 may be referred to as an initial image. As shown in FIG. 11, the thumbnail image 401 may be located above the third image quality adjustment button 303. The image quality of the thumbnail image 401 does not change even if the image quality of the thumbnail images of the first to fifth image quality adjustment buttons 301-305 change by pressing to select any of the first to fifth image quality adjustment buttons 301-305, and the touch command screen 104 displays the image at the start of image quality adjustment as the thumbnail image 401. Also, no function is assigned to the thumbnail image 401 in the third modification of the present embodiment. Thus, even if the user presses the thumbnail image 401, the image quality of the other thumbnail images of the first to fifth image quality adjustment buttons 301-305 does not change.

As described above, since the medical image diagnosis system 100 according to the third modification displays the thumbnail image 401, which is the image at the start of image quality adjustment, on the image quality adjustment setting screen W20, the user may easily compare how the image quality of the image has changed after starting the image quality adjustment.

The present modification was described as a modification for the second embodiment described above but may be also applied to the first or third embodiment.

Other Modifications on the First to Third Embodiments

Likewise, the image processing in the first to third embodiments described above is premised on enhancement image processing with multiresolution decomposition processing and nonlinear anisotropic diffusion filters, but image processing or signal processing may involve any of a linear spatial filter, median filter, input/output curve processing, and gain adjustment processing.

Likewise, the image quality indicators for optimization in the first to third embodiments described above was premised on image processing parameters or indicators that are convertible into parameters in the image processor 204, but the image quality indicators for optimization is not limited to these. In the transmitter/receiver 201 of the medical image diagnosis system 100, the transmitting/receiving condition of the changeable ultrasonic waves relating to the image quality includes a transmission waveform (wave number and frequency), a reception center frequency, a reception frequency band, a reception aperture, and a sound velocity within the subject preset for received signal processing. Thus, the image quality indicators for optimization may include a resolution of at least any of the transmission waveform (wave number and frequency), the reception center frequency, the reception frequency band, the reception aperture, and the sound velocity within the subject preset for received signal processing controlled in the transmitter/receiver 201 of the medical image diagnosis system 100.

Likewise, in the first to third embodiment described above, the image quality depends on a depth of the subject since the ultrasonic signal receives and processes the received signal from the subject. Thus, a uniformity of image quality may be expected by setting each image quality indicator described above for each depth. Therefore, the medical image diagnosis system 100 may perform optimization of image quality by preparing a different image quality indicator for each depth.

Fourth Embodiment

Although the medical image diagnosis system 100 according to the first to third embodiments described above was described with an example configured by the ultrasonic diagnosis system, the image quality optimization process described above is not limited to the ultrasonic diagnosis system and may be applied to various medical diagnosis systems. There, in a fourth embodiment, the medical image diagnosis system 100 will be described with an example applied to an MRI system.

Figure 12:
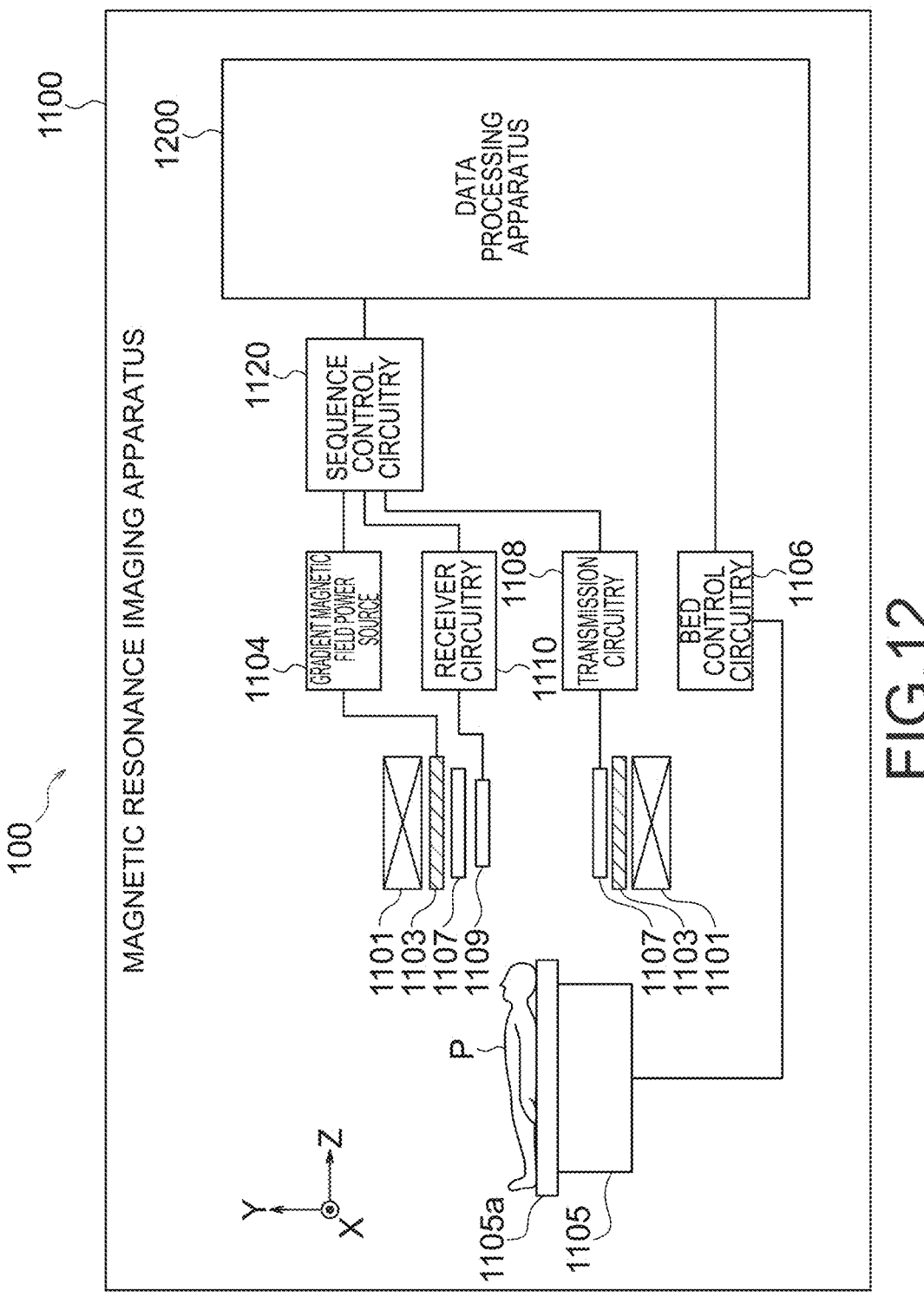
FIG. 12 is a diagram schematically describing a configuration of the medical image diagnosis system according to a fourth embodiment.

FIG. 12 is a diagram schematically describing a configuration of the medical image diagnosis system 100 according to the fourth embodiment. As shown in FIG. 12, in the present embodiment, the medical image diagnosis system 100 is configured by the MRI system 1100. The medical image diagnosis system 100 configured by the MRI system 1100, for instance, is configured by a static magnetic field magnet 1101, a static magnetic field power source (not shown), a gradient magnetic field coil 1103, a gradient magnetic field power source 1104, a bed 1105, a bed control circuitry 1106, a transmission coil 1107, a transmission circuitry 1108, a receiver coil 1109, a receiver circuitry 1110, a sequence control circuitry 1120, and a data processing apparatus 1200. Note that a subject P (e.g., a human) is shown for ease of understanding and not included in the configuration of the MRI system 1100.

The static magnetic field magnet 1101 is a magnet formed in a substantially cylindrical hollow shape and generates a static magnetic field in an inner space. The static magnetic field magnet 1101, for instance, is a superconductive magnet etc., which excites receiving a current supply from the static magnetic field power source. The static magnetic field power source supplies current to the static magnetic field magnet 1101. In another example, the static magnetic field magnet 1101 may be a permanent magnet, in which case the MRI system 1100 may not comprise the static magnetic field power source. Likewise, the static magnetic field power source may be provided aside from the MRI system 1100.

The gradient magnetic field coil 1103 is a coil formed in a substantially cylindrical hollow shape which is arranged on an interior of the static magnetic field magnet 1101. The gradient magnetic field coil 1103 is formed by combining three coils corresponding to each of the X, Y, and Z-axis orthogonal to each other, and these three coils each receive the current supply from the gradient magnetic field power source 1104 and generate a gradient magnetic field which a magnetic field strength changes along each of the X, Y, and Z-axis. The gradient magnetic field of each of the X, Y, and Z-axis generated by the gradient magnetic field coil 1103 may be a slice gradient magnetic field Gs, a phase encoding gradient magnetic field Ge, and a readout gradient magnetic field Gr. The gradient magnetic field power source 1104 supplies current to the gradient magnetic field coil 1103.

The bed 1105 comprises a top board 1105a on which the subject P is placed, and under the control of the bed control circuitry 1106, inserts the top board 1105 into a hollow space (imaging opening) of the gradient magnetic field coil 1103 in a state in which the subject is placed. Generally, the bed 1105 is installed in such a way that the longitudinal direction thereof is parallel to a central axis of the static magnetic field magnet 1101. The bed control circuitry 1106 moves the top board 1105a in the longitudinal direction and a vertical direction by driving the bed 1105 under the control of the data processing apparatus 1200.

The transmission coil 1107 is arranged on the interior of the gradient magnetic field coil 1103 and generates a high-frequency magnetic field by receiving an RF pulse supply from the transmission circuitry 1108. The transmission circuitry 1108 supplies the RF pulse corresponding to a Larmor frequency determined by a type of target atom and the magnetic field strength.

The receiver coil 1109 is arranged on the interior of the gradient magnetic field coil 1103 and receives a magnetic resonance signal emitted from the subject P by an effect of the high-frequency magnetic field. The receiver coil 1109 outputs the received magnetic resonance signal to the receiver circuitry 1110 when it receives the magnetic resonance signal.

The transmission coil 1107 and the receiver coil 1109 are merely examples. It is possible to configure the transmission coil 107 and the reception coil 109 by selecting one or combining two or more from among: a coil having only the transmitting function; a coil having only the receiving function; and a coil having the transmitting and receiving functions.

The receiver circuitry 1100 detects the magnetic resonance signal output from the receiver coil 1109 and generates the magnetic resonance data based on a detected magnetic resonance signal. Specifically, the receiver circuitry 1110 generates the magnetic resonance data by digital converting the magnetic resonance signal output from the receiver coil 1109. Likewise, the receiver circuitry 1100 transmits the generated magnetic resonance data to the sequence control circuitry 1120. Note that the receiver circuitry 1110 may be provided on a gantry apparatus side which comprises the static magnetic field magnet 1101 or the gradient magnetic field coil 1103 etc.

The sequence control circuitry 1120 performs imaging the subject P by driving the gradient magnetic field power source 1104, the transmission circuitry 1108, and the receiver circuitry 1110, based on a sequence information transmitted from the data processing apparatus 1200. Here, the sequence information is information which defines a process to perform imaging. In the sequence information, a strength of current which the gradient magnetic field power source 1104 provides to the gradient magnetic field coil 1103 or a timing of supplying the current, a strength of RF pulse or a timing of applying the RF pulse which the transmission circuitry 1108 provides to the transmission coil 1107, or a timing of the receiver circuitry 1110 detecting the magnetic resonance signal, etc., are defined.

Furthermore, the sequence control circuitry 1120, when it receives the magnetic resonance data from the receiver circuitry 1110 as a result of imaging the subject P by driving the gradient magnetic field power source 1104, the transmission circuitry 1108, and the receiver circuitry 1110, transmits the received magnetic resonance data to the data processing apparatus.

Figure 13:
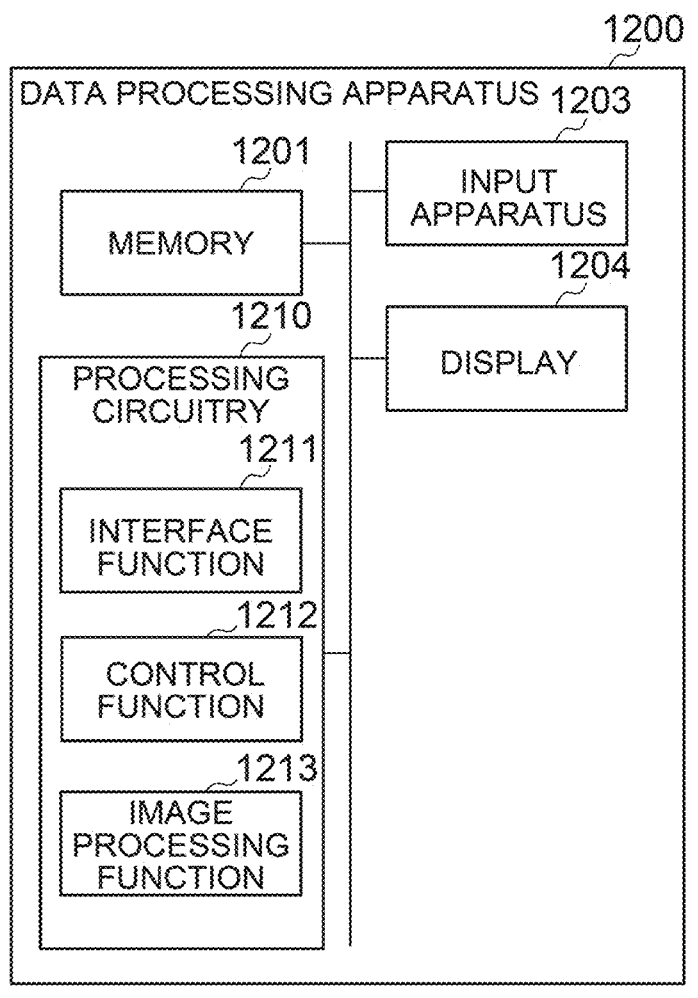
FIG. 13 is a functional block diagram describing functions of the controller of the medical image diagnosis system according to the fourth embodiment.

The data processing apparatus 1200 performs an overall control of the MRI system 1100 and processing the signal received from the sequence control circuitry 1120. The data processing apparatus 1200, as shown in FIG. 13, comprises a processing circuitry 1210, a memory 1201, an input apparatus 1203, and a display 1204. The processing circuitry 1210 comprises an interface function 1211, a control function 1212, and an image processing function 1213.

In the present embodiment, each processing function executed in the interface function 1211, the control function 1212, and the image processing function 1213 are stored in the memory 1201 in the form of computer executable program. The processing circuitry 1210 is a processor which realizes functions corresponding to each program by reading and executing programs from the memory 1201. In other words, the processing circuitry 1210 in a state which has read each program will have each function shown in the processing circuitry 1210.

The processing circuitry 1210 transmits the sequence information to the sequence control circuitry 1120 and receives the magnetic resonance data from the sequence control circuitry 1120 by the interface function 1211. Likewise, when the processing circuitry 1210 receives the magnetic resonance data, the processing circuitry 1210 which has the interface function 1211 stores the received magnetic resonance data in the memory 1201.

The magnetic resonance data stored in the memory 1201 is arranged in a k-space by the control function 1212. As a result, the memory 1201 stores a k-space data.

The memory 1201 stores the magnetic resonance data received by the processing circuitry 1210 which has the interface function 1211, the k-space data arranged in the k-space by the processing circuitry 1210 which has the control function 1212, and image data generated by the processing circuitry 1210 which has the image processing function 1213, etc.

The processing circuitry 1210 performs an overall control of the MRI system 1100 by the control function 1212 to control an imaging, an image generation, or an image display etc. For instance, the processing circuitry 1210 which has the control function 1212 receives the input of an imaging condition (imaging parameters etc.) on the GUI and generates the sequence information according to the received imaging condition. Likewise, the processing circuitry 1210 which has the control function 1212 transmits the generated sequence information to the sequence control circuitry 1120.

The processing circuitry 1210 reads the k-space data from the memory 1201 by the image processing function 1213 and generates the magnetic resonance image by applying a reconstruction processing, such as a Fourier transform, to the read k-space data. Likewise, the image processing function 1213 also performs the enhancement image processing according to the first embodiment.

The processing circuitry 1210 obtains data or image etc. for image processing with the image processing function 1213, by the interface function 1211 from the memory 1201.

The input apparatus 1203 receives various commands or information input from an operator. The input apparatus 1203, for example, is a pointing device such the mouse or the trackball, a selecting device such as a mode selector switch, or the input device such as the keyboard. The input apparatus 1203 also comprises the touch command screen formed by the display 1204 which will be described later.

The display 1204, under the control of the control function 1212 etc., displays the GUI to receive the input of imaging conditions or the images generated by the control function 1212. The display 1204, for example, is a display device such as a liquid crystal display. The display 1204 is one example of the display. The display 1204 may comprise the mouse, the keyboard, the button, a panel switch, the touch command screen, a foot switch, the trackball, or the joystick, etc.

Also, like in the ultrasonic diagnosis system described in the first to third embodiments, in the MRI system 1100 as described above, it is possible to change the value of the image quality indicator and to adjust image quality of the medical image by executing image quality optimization process shown in FIG. 5.

In such case, the target medical image to adjust the values of the image quality indicators becomes an MRI image reconstructed from k-space data. For instance, like in the ultrasonic diagnosis system, the image quality indicators of the MRI image form the image quality adjustment setting screen W10, W20, W30 as shown in the first to third embodiments described above on the touch command screen 104 on the display 1204, as the GUI to adjust the values of the image quality indicators with the image processing function 1213.

Other than the fact that the thumbnail images displayed on each image quality adjustment button are generated based on MRI images, the operations and display formats of the image quality adjustment setting screens W10, W20, and W30 are equivalent to that of the first to third embodiments described above. In other words, the image quality optimization process shown in FIG. 5 is executed in the processing circuitry 1210, setting the values of the image quality indicators with the optimal image quality for the user. When the image quality optimization process is executed, the image processing function 1213 functions as the first image generation function 206a, the first image display function 206b, the second image generation function 206c, the second image display function 206d, and the new image quality indicator calculating function 206e, and the control function 1212 functions as the regeneration display function 206f.

As described above, it is possible to configure the medical image diagnosis system 100 with the MRI system 1100 according to the medical image diagnosis system 100 according to the present embodiment. As such, the values of image quality indicator may be adjusted for medical images captured in various medical image diagnosis systems such as the ultrasonic diagnosis system, the MRI system, an X-ray Computed Tomography (CT) system, and a Positron Emission Tomography (PET) system.

Note that the word "processor" used in above descriptions means circuits such as, for example, a Central Processing Unit (CPU), a Graphics Processing Unit (GPU), an Application Specific Integrated Circuit (ASIC), a programmable logic device (for example, a Simple Programmable Logic Apparatus (SPLD), a Complex Programmable Logic Apparatus (CPLD), and a Field Programmable Gate Array (FPGA)). The processor executes functions by reading and executing programs stored in the memory. Note that programs may be configured to be directly integrated in the processor instead of being storing in the memory. In this case, the processor realizes functions by reading and executing programs stored in the circuit. Note that the processor is not limited to the case arranged as a single processor circuit, but may be configured as a single processor by combining a plurality of independent circuits to realize functions. Furthermore, a plurality of component elements in FIG. 3 may be integrated into one processor to realize the functions.

While certain embodiments have been described, these embodiments have been presented by way of example only and are not intended to limit the scope of the inventions. The embodiments may be in a variety of other forms. Furthermore, various omissions, substitutions and changes may be made without departing from the spirit of the inventions. The embodiments and their modifications are included in the scope and the subject matter of the invention, and at the same time included in the scope of the claimed inventions and their equivalents.

For the embodiments described above, following notes are disclosed as one aspect and alternative features of the invention.

Note 1

A medical image diagnosis system comprises processing circuitry configured to:

set values of an image quality indicator selected by a user regarding multiple types of the image quality indicator to display a medical image as an anchor, and generate a thumbnail image of the medical image based on the anchor as a first thumbnail image;

cause a display to display the first thumbnail image;

generate a plurality of thumbnail images as second thumbnail images by respectively increasing or decreasing the multiple types of the image quality indicator from the anchor regarding the medical image;

cause the display to display the plurality of second thumbnail images;

allow the user to select one of the first thumbnail image and the plurality of second thumbnail images, and calculate a new image quality indicator adjusted with a variable step width based on the selected one of the first thumbnail image and the plurality of the second thumbnail images; and generate a new first thumbnail image by using the values of the image quality indicators corresponding to the selected one of the first thumbnail image and the plurality of the second thumbnail images selected by the user as a new anchor, display the new first thumbnail image, generate a plurality of new second thumbnail images based on the values of the new image quality indicator, and display the plurality of new second thumbnail images.

Note 2

The processing circuitry may be further configured to generate a composed image based on the image quality indicator composed by respectively increasing or decreasing the multiple types of the image quality indicator from the anchor as one of the plurality of second thumbnail images; and

Note 3

The processing circuitry may be further configured to display the composed image as one of the plurality of second thumbnail images on the display.

Note 4

The processing circuitry may be further configured to switch increasing or decreasing the new image quality indicator based on a user operation.

Note 5

The calculation of the new image quality indicator may depend on a probability selecting the one of the first thumbnail image and the plurality of second thumbnail images using a Bradley-Terry-Luce (BTL) model or a Thurstone-Mosteller model.

Note 6

The calculation of the new image quality indicator may be optimized by a probabilistic inference using Bayes' theorem, and the optimized calculation may be performed by maximizing an acquisition function.

Note 7

The probabilistic inference using Bayes' theorem may be performed by a prior distribution model following a Gaussian process.

Note 8

The processing circuitry may be further configured to:

calculate a plurality of parameters from the values of the image quality indicator;

perform image processing or signal processing based on the calculated plurality of parameters; and generate the first thumbnail image and the plurality of second thumbnail images, respectively.

Note 9

The image processing or the signal processing may be any one of multiresolution decomposition processing, nonlinear anisotropic diffusion filter, linear spatial filter, median filter, input/output curve processing, and gain adjustment processing.

Note 10

The medical image may be an image captured by an ultrasonic diagnosis system.

Note 11

The processing circuitry may be further configured to:

calculate a plurality of parameters from the values of the image quality indicator, perform ultrasonic transmission/reception under condition of the calculated plurality of parameters; and generate the first thumbnail image and the second thumbnail image respectively.

Note 12

The condition of the ultrasonic transmission/reception is any one of a transmission waveform, a reception center frequency, a reception frequency band, a reception aperture, and a sound velocity.

Note 13

In the ultrasonic diagnosis system, the image quality indicator may be optimized for each depth of a subject.

Note 14

The multiple types of the image quality indicator may include any one of a noise reduction, an edge enhancement, a coherency enhancement, an edge detectability, a brightness, a contrast, a gain, a high brightness enhancement, and a resolution.

Note 15

The number of the second thumbnail images may be greater than the number of types of the image quality indicator.

Note 16

A control method of a medical image diagnosis system comprises:

setting values of image quality indicator selected by a user regarding multiple types of the image quality indicator to display a medical image as an anchor, and generates a thumbnail image of the medical image based on the anchor as a first thumbnail image;

causing the display to display the first thumbnail image;

generating a plurality of thumbnail images as second thumbnail images by respectively increasing or decreasing the multiple types of the image quality indicator from the anchor regarding the medical image;

causing the display to display the plurality of second thumbnail images;

allowing the user to select one of the first thumbnail image and the plurality of second thumbnail images, and calculating a new image quality indicator adjusted with a variable step width based on the selected one of the first thumbnail image or the plurality of the second thumbnail images; and generating a new first thumbnail image by using the values of the image quality indicator corresponding to selected the one of the first thumbnail image and the second thumbnail image selected by the user as a new anchor, causing the display to display a new first thumbnail image, generating a plurality of new second thumbnail images based on the values of the new image quality indicator, and causing the display to display the plurality of new second thumbnail images.

The invention claimed is:

1. A medical image diagnosis system, comprising:
processing circuitry configured to:
set values of an image quality indicator selected by a user regarding multiple types of the image quality indicator to display a medical image as an anchor, and generate a thumbnail image of the medical image based on the anchor as a first thumbnail image;

cause a display to display the first thumbnail image;

generate a plurality of thumbnail images as second thumbnail images by respectively increasing or decreasing the multiple types of the image quality indicator from the anchor regarding the medical image;

cause the display to display the plurality of second thumbnail images;

allow the user to select one of the first thumbnail image and the plurality of second thumbnail images, and calculate a new image quality indicator adjusted with a variable step width based on the selected one of the first thumbnail image and the plurality of the second thumbnail images;

generate a new first thumbnail image by using the values of the image quality indicators corresponding to the selected one of the first thumbnail image and the plurality of the second thumbnail images selected by the user as a new anchor, display the new first thumbnail image, generate a plurality of new second thumbnail images based on the values of the new image quality indicator, and display the plurality of new second thumbnail images;

generate a composed image based on the image quality indicator composed by respectively increasing or decreasing the multiple types of the image quality indicator from the anchor as one of the plurality of second thumbnail images; and display the composed image as one of the plurality of second thumbnail images on the display; and buttons configured to change the image quality indicator.

2. The medical image diagnosis system according to claim 1, wherein:
the buttons include an increasing button for increasing the image quality indicator and a decreasing button for decreasing the image quality indicator; and the processing circuitry is further configured to increase or decrease the new image quality indicator based on a user operation on the increase button or the decrease button.

3. The medical image diagnosis system according to claim 1, wherein the calculation of the new image quality indicator is optimized by a probabilistic inference using Bayes' theorem, and the optimized calculation is performed by maximizing an acquisition function.

4. The medical image diagnosis system according to claim 3, wherein the probabilistic inference using Bayes' theorem is performed by a prior distribution model following a Gaussian process.

5. The medical image diagnosis system according to claim 1, wherein the processing circuitry is further configured to:
calculate a plurality of parameters from the values of the image quality indicator;

perform image processing or signal processing based on the calculated plurality of parameters; and generate the first thumbnail image and the plurality of second thumbnail images, respectively.

6. The medical image diagnosis system according to claim 5, wherein the image processing or the signal processing is any one of multiresolution decomposition processing, non-linear anisotropic diffusion filter, linear spatial filter, median filter, input/output curve processing, and gain adjustment processing.

7. The medical image diagnosis system according to claim 1, wherein the medical image is an image captured by an ultrasonic diagnosis system.

8. The medical image diagnosis system according to claim 7, wherein the processing circuitry is further configured to:
calculate a plurality of parameters from the values of the image quality indicator, perform ultrasonic transmission/reception under condition of the calculated plurality of parameters; and generate the first thumbnail image and the second thumbnail image, respectively.

9. The medical image diagnosis system according to claim 8, wherein the condition of the ultrasonic transmission/reception is any one of a transmission waveform, a reception center frequency, a reception frequency band, a reception aperture, and a sound velocity.

10. The medical image diagnosis system according to claim 7, wherein, in the ultrasonic diagnosis system, the image quality indicator can be optimized for each depth of a subject.

11. The medical image diagnosis system according to claim 7, wherein the processing circuitry is configured to calculate the new image quality indicator based upon a change indicated by operation of one of the buttons.

12. The medical image diagnosis system according to claim 1, wherein the multiple types of the image quality indicator include any one of a noise reduction, an edge enhancement, a coherency enhancement, an edge detectability, a brightness, a contrast, a gain, a high brightness enhancement, and a resolution.

13. The medical image diagnosis system of claim 1, wherein a number of the second thumbnail images is greater than a number of types of the image quality indicator.

14. A medical image diagnosis system, comprising: processing circuitry configured to:

set values of an image quality indicator selected by a user regarding multiple types of the image quality indicator to display a medical image as an anchor, and generate a thumbnail image of the medical image based on the anchor as a first thumbnail image;

cause a display to display the first thumbnail image;

generate a plurality of thumbnail images as second thumbnail images by respectively increasing or decreasing the multiple types of the image quality indicator from the anchor regarding the medical image;

cause the display to display the plurality of second thumbnail images;

allow the user to select one of the first thumbnail image and the plurality of second thumbnail images, and calculate a new image quality indicator adjusted with a variable step width based on the selected one of the first thumbnail image and the plurality of the second thumbnail images; and generate a new first thumbnail image by using the values of the image quality indicators corresponding to the selected one of the first thumbnail image and the plurality of the second thumbnail images selected by the user as a new anchor, display the new first thumbnail image, generate a plurality of new second thumbnail images based on the values of the new image quality indicator, and display the plurality of new second thumbnail images, wherein the calculation of the new image quality indicator depends on a probability selecting the one of the first thumbnail image and the plurality of second thumbnail images using a Bradley-Terry-Luce (BTL) model or a Thurstone-Mosteller model.

15. A control method of a medical image diagnosis system, comprising:

setting values of image quality indicator selected by a user regarding multiple types of the image quality indicator to display a medical image as an anchor, and generates a thumbnail image of the medical image based on the anchor as a first thumbnail image;

causing the display to display the first thumbnail image;

generating a plurality of thumbnail images as second thumbnail images by respectively increasing or decreasing the multiple types of the image quality indicator from the anchor regarding the medical image;

causing the display to display the plurality of second thumbnail images;

allowing the user to select one of the first thumbnail image and the plurality of second thumbnail images, and calculating a new image quality indicator adjusted with a variable step width based on the selected one of the first thumbnail image or the plurality of the second thumbnail images;

generating a new first thumbnail image by using the values of the image quality indicator corresponding to selected the one of the first thumbnail image and the second thumbnail image selected by the user as a new anchor, causing the display to display a new first thumbnail image, generating a plurality of new second thumbnail images based on the values of the new image quality indicator, and causing the display to display the plurality of new second thumbnail images;

generating a composed image based on the image quality indicator composed by respectively increasing or decreasing the multiple types of the image quality indicator from the anchor as one of the plurality of second thumbnail images;

displaying the composed image as one of the plurality of second thumbnail images on the display; and changing the image quality indicator by operating buttons for changing the image quality indicator.

* * * * *